United States Patent [19]

Schmid

[11] 4,108,166
[45] Aug. 22, 1978

[54] CARDIAC FREQUENCY MEASURING INSTRUMENT

[76] Inventor: Walter Schmid, Bahnhofstrasse 7 - 9, D 8870 Günzburg, Fed. Rep. of Germany

[21] Appl. No.: 687,708

[22] Filed: May 19, 1976

[51] Int. Cl.² ............................................. A61B 5/02
[52] U.S. Cl. ............................. 128/2.06 F; 128/2.05 T
[58] Field of Search .................. 128/2.06 F, 2.06 A, 128/2.06 B, 2.06 G, 2.06 R, 2.05 P, 2.05 T, 2.05 R, 419 P; 58/152 R

[56] References Cited

U.S. PATENT DOCUMENTS

| | | | |
|---|---|---|---|
| 2,848,992 | 8/1958 | Pigeon | 128/2.06 F |
| 3,144,018 | 8/1964 | Head | 128/2.06 R X |
| 3,703,900 | 11/1972 | Holznagel | 128/2.06 F X |
| 3,803,834 | 4/1974 | Reese | 58/152 R |
| 3,805,796 | 4/1974 | Terry, Jr. et al. | 128/419 P |
| 3,828,768 | 8/1974 | Douglas | 128/2.06 A |
| 3,861,387 | 1/1975 | Lawhorn et al. | 128/2.06 A |
| 3,927,663 | 11/1975 | Russell et al. | 128/2.06 A |
| 3,938,507 | 2/1976 | Sarnoff et al. | 128/2.06 B |
| 3,948,250 | 4/1976 | Weisman | 128/2.06 F |
| 3,953,848 | 4/1976 | Dillman et al. | 128/2.06 R X |
| 3,972,320 | 8/1976 | Kalman | 128/2.05 P X |
| 3,978,849 | 9/1976 | Geneen | 128/2.05 T |
| 4,030,483 | 6/1977 | Stevens | 128/2.05 T |

FOREIGN PATENT DOCUMENTS 2,309,467  8/1974  Fed. Rep. of Germany ...... 128/2.06 F

OTHER PUBLICATIONS

"A New Instantaneous Ratemeter," Methods & Instrumentation In Med. Eng., 1972.
"Heartbeat Totalizer," Waters Product Data, 1965.

*Primary Examiner*—Lee S. Cohen
*Attorney, Agent, or Firm*—Price, Heneveld, Huizenga & Cooper

[57] ABSTRACT

The specification describes a cardiac frequency measuring instrument which has a frequency measuring device to be carried on the arm of a user. A cable connects the measuring instrument with measuring electrodes carried on the body and with an optical display for the measured heart frequency. There is a miniaturized digital circuit accommodated in the housing having the size of a wrist watch with a minimum electrical power* for the digital measurement and display of the cardiac frequency. Use is made of a resonant amplifier, connected as a high pass filter, for suppressing the amplification and display of motional artefacts.

*consumption or dissipation

14 Claims, 6 Drawing Figures

CARDIAC FREQUENCY MEASURING INSTRUMENT

BACKGROUND OF INVENTION (1) Field to Which Invention Relates

The invention relates to a heart frequency measuring instrument with a frequency measuring device to be carried on the arm, with a cable connecting the measuring instrument with measuring electrodes carried on the body and with an optical display for the measured heart frequency.

(2) The Prior Art

Such a heart frequency measuring instrument or cardiotachometer is described for example in the German Patent Specification (Offenlegungsschrift) No. 2,309,467 and comprises an analog computer accommodated in the housing, which is connected with two electrodes fixed to the thorax of the patient, calculates the heart frequency in heart beats per minute and displaces the calculated value on a tacho instrument with a scale. The device described in this case is however subject to a whole series of disadvantages. On the one hand the computer connected with a 9 volt battery voltage is an analog computer, which generally has a substantial energy requirement so that the batteries used often have to be replaced and on the other hand the device described in the specification has a substantial weight, which is a nuisance for the user, since the device should, to be properly used, be worn all the time. Another serious disadvantage lies in the size of the device specified which is about as long as a human hand and impairs the freedom of movement to the user. More particularly however the device in the above mentioned German patent specification is liable to attract attention owing to its size in the exposed position in which it is carried on the wrist and it will be a source of undesired curiosity on the part of strangers. Such an effect is more particularly undesirable, since the users are usually persons with cardiac complaints and convalescent persons, who must keep a watch on their cardiac activity and should not be exposed to any psychological strain.

Furthermore there has already been a proposal to provide a device for measuring the cardiac frequency which comprises a battery operated amplifier, accommodated in a box-shaped housing. Furthermore there are three stick-on electrodes, connected with the amplifier via separate cables, for producing an electrocardiogram and there is a wrist watch device, connected via three cables with the amplifier housing, for displaying the heart frequency measured by means of a suitable pointer-type display. Such a device however also suffers from a series of disadvantages, since it has an undesirably large number of individual components, which must be accommodated at different positions on the body and, respectively in the clothing and must be connected respectively with each other by means of three cables in each case. Furthermore the battery operated amplifier only runs for 72 hours with one battery charge and the spring driven watch device must be wound up every 24 hours. While the box comprising the current supply and the amplifier is to be carried with the computer and with the pulse generator in the pocket, the watch device, which only serves for indicating the cardiac frequency measured, has to be carried on the arm and furthermore does not have any safety devices which would provide an indication of a particularly low or particularly high cardiac frequency. Added to this one must consider that the large number of individual parts represents a nuisance for the patient and that the electrodes, which have to be connected via cables with the amplifier to be carried in the pocket have the tendency to detach themselves, since the cables are passed through articles of clothing to the amplifier.

SUMMARY OF INVENTION

One aim of the present invention is that of affording a construction of a cardiac frequency measuring instrument with a frequency measuring device, to be carried on the arm, which has all measuring and monitoring means and does not cause any spurious pulses to be displayed.

In the context of a cardiac frequency measuring instrument with a frequency measuring device to be carried on the arm, with a cable connecting the measuring instrument with measuring electrodes carried on the body and with an optical display for the measured heart frequency the invention provides a miniaturised digital circuit accommodated in a housing having the size of a wrist watch, with a minimum electrical power consumption or dissipation for digital measurement and display of the cardiac frequency, which has a resonant amplifier, connected as a high pass filter, for suppressing the amplification and display of motional artefacts.

In accordance with a further development of the invention the housing or the arm strap of wrist watch are constructed as a neutral electrode.

It is particularly advantageous if the digital circuit comprises a digital display device with display elements, produced in LCD-technology, for a numerical display of frequency data, in the case of which the digital display elements can indicate a decrease of the operational voltage below a predetermined threshold voltage with a decrease in luminosity.

Conveniently in addition to the digital circuit there is a circuit for driving a display with at least one point, which in the measured systolic rhythm of the heart frequency is switched on and the flashing point or points are preferably located between the hundreds and the tens digits of the numerical display.

In accordance with a further feature of the invention the digital circuit has an alarm device adapted to respond to an upper and a lower limiting frequency, which gives rise to an acoustic signal when a value occurs coming below or above the limiting frequency; the values for the two limiting frequencies are in this case capable of being set to any integral values between 0 and 255 including 0.

It is particularly advantageous if the digital circuit has a reed contact, adapted to be closed by an external magnet, for setting the lower and upper limiting frequency, and which during the presence of the respective magnet drives a clock generator, sets registers storages and counters at zero and with a predetermined clock beat produces a continuous pulse sequence for counting frequency values of a circuit, and the last counted frequency value is stored as a limiting frequency in a storage or memory.

In the case of another preferred embodiment of the invention the digital circuit is equipped with two respectively mechanically operated micro-key-switches, serving for setting the lower and upper limiting frequency, which on actuation or depressing of the respective key-switch drive a clock generator, set registers, storages and counters at zero and with a pre-established clock beat produce a continuous pulse sequence for counting frequency values of a circuit so that the last frequency value counted is stored as a limiting frequency in the respective limiting frequency storage.

Conveniently on setting the limiting frequencies the measuring device for external signals is switched off and the digital circuit actuates a circuit connected with the digital display which displays the last respective frequency value counted; furthermore the alarm device is conveniently switched off during the setting of the limiting frequencies.

In accordance with a further embodiment of the invention in the case of the absence of input pulses at the input amplifier after a pre-established time interval the digital circuit is automatically switched over to standby operation, in which its power requirement only amounts to a fraction of the normal operational power requirement.

It is particularly advantageous if the digital circuit of the cardiac frequency measuring instrument is constructed using components made in C-MOS-technology and if its voltage supply system comprises mercury cells keeping a constant voltage over long periods of time.

The cardiac frequency measuring instrument in accordance with the invention accommodated in the housing of a wrist watch is connected with an integrated battery set with a period of service of approximately 6 months in the case of continuous operation and indicates the instantaneous cardiac frequency with numbers and in addition to being a source of comfort for the user flashes in step with the cardiac rhythm and shows that the device is still functioning even if the cardiac frequency does not vary.

In order to record the electrocardiogram (ECG) the input amplifier of the digital circuit is connected capacitively with the input electrodes so that on the basis of the galvanic separation no static current flows via the electrodes. The digital circuit is conveniently made up of C-MOS or Cosmos circuits, in the case of which the error rate due to digitalisation is kept low. Since the cardiac frequency measuring instrument, owing to direct contact with the human body, is not subjected to any large variations in temperature and the current supply using, preferably, mercury cells is relatively constant in potential, the overall error amounts to ± 1% for up to 120 beats per minute and rises linearly to a value of ± 2.5% at 240 beats per minute.

All components of the cardiac frequency measuring instrument are designed for providing a lower power consumption and the longest possible permanent use while ensuring reliability of the cardiac frequency measuring instrument in accordance with the invention; for displaying the cardiac frequency measured liquid crystal elements in so-called LCD-technology are employed, while micropower operational amplifiers form the input amplifier, which converts the analog 1 millivolt QRS-complex of the electrocardiogram, sensed by the two external electrodes into a rectangular signal with a logic level.

The cardiac frequency measuring instrument in accordance with the invention accommodated in a wrist watch housing of normal dimensions is completely inconspicuous owing to its shape and size even if the user does not during summer weather conditions wear any jacket or the like.

DESCRIPTION OF PREFERRED EMBODIMENTS OF THE INVENTION

The cardiac frequency measuring instrument in accordance with the invention is now to be described in more detail with reference to embodiments and on the basis of the drawings.

Figure 1:
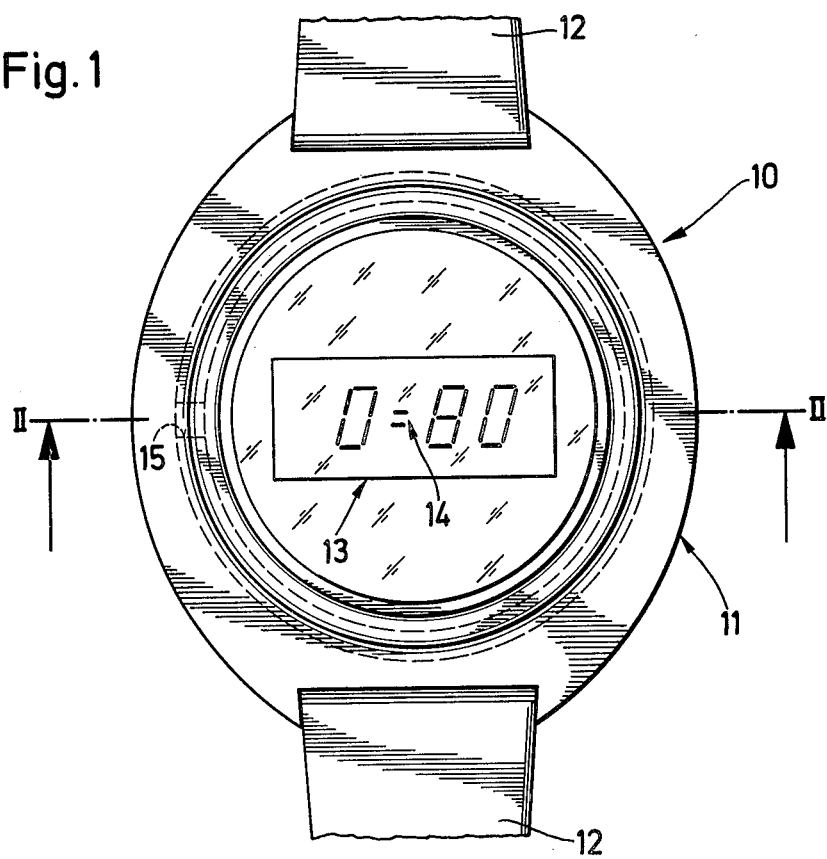
FIG. 1 shows a diagrammatic plan view of the cardiac frequency measuring instrument in accordance with the invention.
Figure 2:
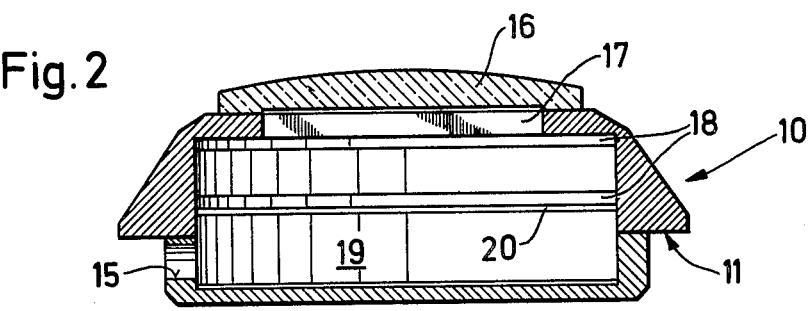
FIG. 2 shows a section through the cardiac frequency measuring instrument along the line II—II of FIG. 1.

FIGS. 1 and 2 show the spatial arrangement of a cardiac frequency measuring instrument 10 diagrammatically. The digital circuit as a whole is accommodated in a wrist watch housing 11, which will conventionally consist of a metal well known for this purpose as for example stainless steel. The housing is provided with a strap 12, which is preferably made of metal and enables the housing to be carried on the arm. In this respect either the housing 11 or the strap 12 or both can serve as the neutral electrode VM for sensing the ECG. As is shown in FIG. 1 the housing 11 has a passage 15 for a patient cable, with which two stick-on electrodes E1 and E2, which can be attached to the thorax of the patient (see FIG. 3) can be connected with the digital circuit of the cardiac frequency measuring instrument. Naturally the passage 15 for the patient cable can also be arranged on the right-hand side of the housing when the device is or has to be carried on the right-hand arm.

On the top side of the housing 11 there is a cover glass 16 lying on top of an optic digital numerical display 13, which makes possible a three digit display of the cardiac frequency in beats per minute. Preferably between the hundreds and tens digits of the numerical display there is a double point 14, which is flashed on in accordance with the systolic rhythm of the cardiac frequency when the cardiac frequency measuring instrument is connected and thus indicates satisfactory functioning of the device in order to reasure the patient, even if the measured in displayed cardiac frequency remains constant for a long period of time. The numerical display 13 consists of liquid crystal elements produced in LDC-technology, which have a low electrical power consumption. The optical indication is arranged directly under the cover glass 16 in a space 17 and above a larger space 18, which accommodates in various electronic planes the circuits of the cardiac frequency measuring instrument. Below the space 18 in a chamber 19 there is a voltage supply unit for the circuits, switch contacts for setting the upper and the lower limiting frequencies, a loudspeaker and also connections for the external electrodes of the patient and between the chamber 19 and the space 18 there is a contact plane 20 for connection of the various units.

The switch contacts for setting the upper and the lower limiting frequencies can be constructed as reed contacts in accordance with a first preferred embodiment of the invention, which can be closed with external magnets for setting the lower and the upper limiting frequencies. Such external magnets can be attached to the wrist strap 12 in a suitable manner. In the case of another preferred embodiment instead of the reed contacts special microkey-switches are employed, which can be actuated using a special U-shaped part or the like by pressing down the microkey-switches, and the actuating U-shaped part can also be attached and carried in a suitable manner on the wrist strap 12. In this manner the user will be in a position at all times to set the limiting frequencies afresh and to adjust them, something which is for example important when high performance athletes use such a cardiac frequency measuring instrument for keeping a watch on their training activities.

In the device an internal storage is provided for the upper and the lower limiting frequencies and an alarm device is accommodated, which provides an acoustic warning signal, lasting for 0.5 seconds when the heart frequency comes below the lower limiting frequency or exceeds the upper one, after approximately ten beats of the heart. This warning signal is repeated until the heart frequency measuring instrument measures a frequency lying between the upper and the lower limiting frequencies.

The setting of the upper and the lower limiting frequencies is carried out in the case of the embodiment shown in the drawings by means of two magnets fixed externally on the device, with which one of the switching contacts, denoted as Reedmax and Reedmin respectively, in the interior of the housing is operated. On closing the switching contact for the upper limiting frequency the display is set at 000 and then the display controlled by the digital circuit counts up with intervals of 0.5 second and each value appearing in the display is accepted in the storage for the upper limiting frequency.

If the switching contact Reedmin which can be closed irrespectively of the switching contact for the upper limiting frequency, is closed which serves for setting the lower limiting frequency the display value is also taken over in the storage for the lower limiting frequency. If the switching contacts are constructed as microkey-switches, the setting of the lower and the upper limiting frequencies is undertaken by actuating or depressing the key-switches with the U-shaped part provided for this purpose. In a similar manner for setting the lower limiting frequency the two microkey-switches are actuated while for setting the upper limiting frequency only the switch indicated as Reedmax is actuated.

In the case of the embodiment reproduced in the drawings and described in detail in what follows the two storages are respectively designed for whole numbers between 0 and 255 and more particularly for the lower limiting frequency also the value 0 itself is stored and accordingly the lower limiting frequency can be practically switched off. The selected range is normally also sufficient for high performance athletes but however it can naturally be enlarged by a suitable extension of the digital circuit.

For measuring the heart frequency an ECG signal with an amplitude of approximately 1 millivolt is sensed via two stick-on electrodes in positions corresponding to the tip of sthe heart and via a capacitively coupled isolating difference amplifier OP1 it is amplified to a value of approximately 100 millivolts; following this the signal is supplied to a resonant amplifier OP2, which amplifies from the ECG the so-called QRS-complex to a value of approximately 1 volt. A trigger amplifier OP3 connected with the output of the resonant amplifier OP2, shapes the analog signal of the QRS-complex to form a rectangular signal with a logic level which is further processed in the following Cosmos logic circuitry.

The cardiac frequency measuring instrument displays the respective cardiac frequency measured in a conventional manner, that is to say in heart beats per minute in the case of which the time between two QRS-complexes serves as a measurement for the respective cardiac frequency. The calculation of the display value is in accordance with the formula $$\text{display value} = 60\,000/t_D$$

in which the display value in heart beats per minute and $t_D$ as the difference in time in milliseconds are taken between two QRS-complexes.

For reasons of accuracy in the case of the embodiment the operation is preferably carried out with the time between three respective QRS-complexes and the time $t_D$ is broken down into blocks each of 8 ms and then summated. The formula for the calculation of the display value takes on the form $$\text{display value} = 15000/t_M$$

with $t_M = 2 \times t_D/8$ in milliseconds.

The bringing into synchronism of the circuit is carried out with the help of two monostable multivibrators or monoflops connected with the trigger amplifier OP3 and arranged in tandem, as denoted by reference numerals M1 and M2. The first monoflop M1 runs over a time interval of 40 milliseconds in order to prevent double actuation by an excessively large QRS-complex. The second monoflop M2 is triggered by the setting of the 40 millisecond interval, then runs for approximately 5 microseconds and via the pulse PA1 resets the time measuring counter ZM to 0.

After the bringing into synchronism of the time measuring circuit to a first QRS-complex the time measuring counter ZM is caused to count with a frequency of 125 Hz in accordance with 8 milliseconds is stopped with a second following QRS-complex. The counted frequency value is stored and supplied to the division counter DiCo.

The calculation of the frequency value from the pulses detected by the electrodes E1 and E2 is carried out in accordance with the above formula after the third QRS-complex with a working frequency of 30 kHz in the division counter DiCo and lasts for 0.5 second corresponding to 15 000 pulses. The result of division is established in the display register AZR and after examination of the division is indicated digitally via the display driver AT. Independently of the calculation of the display of the cardiac frequency value the double points 14 arranged between the hundreds and tens digit of the numerical display are caused to operate and by virtue of their flashing in beat with the heart indicate that the QRS-complex is being detected.

Monitoring of any coming below or coming above of the respective upper and lower limiting frequency is carried out in parallel to the establishment of the results of division in BCD code in the display register AZR by simultaneous summating in a comparison counter GVR operating in binary code.

The setting of the comparison counter GVR is compared via an 8-bit comparator VG as regards identity with the lower cardiac frequency stored in the storage Smin on reaching this value the upper cardiac frequency stored in the storage Smax is switched over and the comparison counter is examined as regards values which are greater than the stored upper limiting frequency value. If the frequency value, which comes to be displayed, lies outside the respective upper and lower limiting frequency values stored, this value is stored in an alarm counter AC. If values coming outside the limiting values occur three times in succession via the loudspeaker LSP an acoustic signal is produced with a duration of approximately 0.5 seconds.

The time measuring circuit ZM, which registers the time between three respective QRS-complexes belonging together is released after finishing and display of the results of division and, respectively, after termination of the alarm for bringing into synchronisation for the next QRS-complex so that a new time measuring calculating cycle begins.

If in the digital circuit after termination of a computing cycle after approximately 16 seconds no new synchronisation occurs or if between three QRS-complexes the length of this time interval is exceeded, the digital circuit is switched over to standby operation and the digital display is switched out and the supply current level of the circuit is reduced to approximately 50% of the operating current level.

The setting of the lower and the upper limiting frequencies is preferably carried out during standby operation, that is to say when the input electrodes are removed. In accordance with the type of the above mentioned switching contacts the setting of the limiting frequencies is started by closing the switching contact Reedmax either with an externally applied magnet or with a suitable U-shaped part. The closing of the switching contact Reedmax brings about starting of the clock generator TG, a setting at 0 of the display register AZR, the display storage AT, the comparison counter GVR and the storage Smax for the upper limiting frequency.

There now begins a continuous scaling or counting up of the display with a 0.5 second rhythm, and each frequency value accepted in the display storage AT also passes to the storage Smax. If the switching contact Reedmin is also closed, the respective frequency value is also accepted in the storage Smin for the lower limiting frequency. During the setting of the limiting frequencies the alarm device is switched off and the provision of an alarm signal will not be possible.

The setting of the limiting frequencies is undertaken in four steps: Closing of the switching contacts with a magnet or an U-shaped part at the suitably marked parts on the housing of the cardiac frequency measuring instrument, observation of counting up on the numerical display, removal of the magnet or of the U-shaped part for the setting of the lower limiting frequency immediately after reaching the desired limiting frequency value and removal of the magnet or U-shaped part for setting the upper limiting frequency immediately after reaching the upper limiting frequency value.

Figure 3:
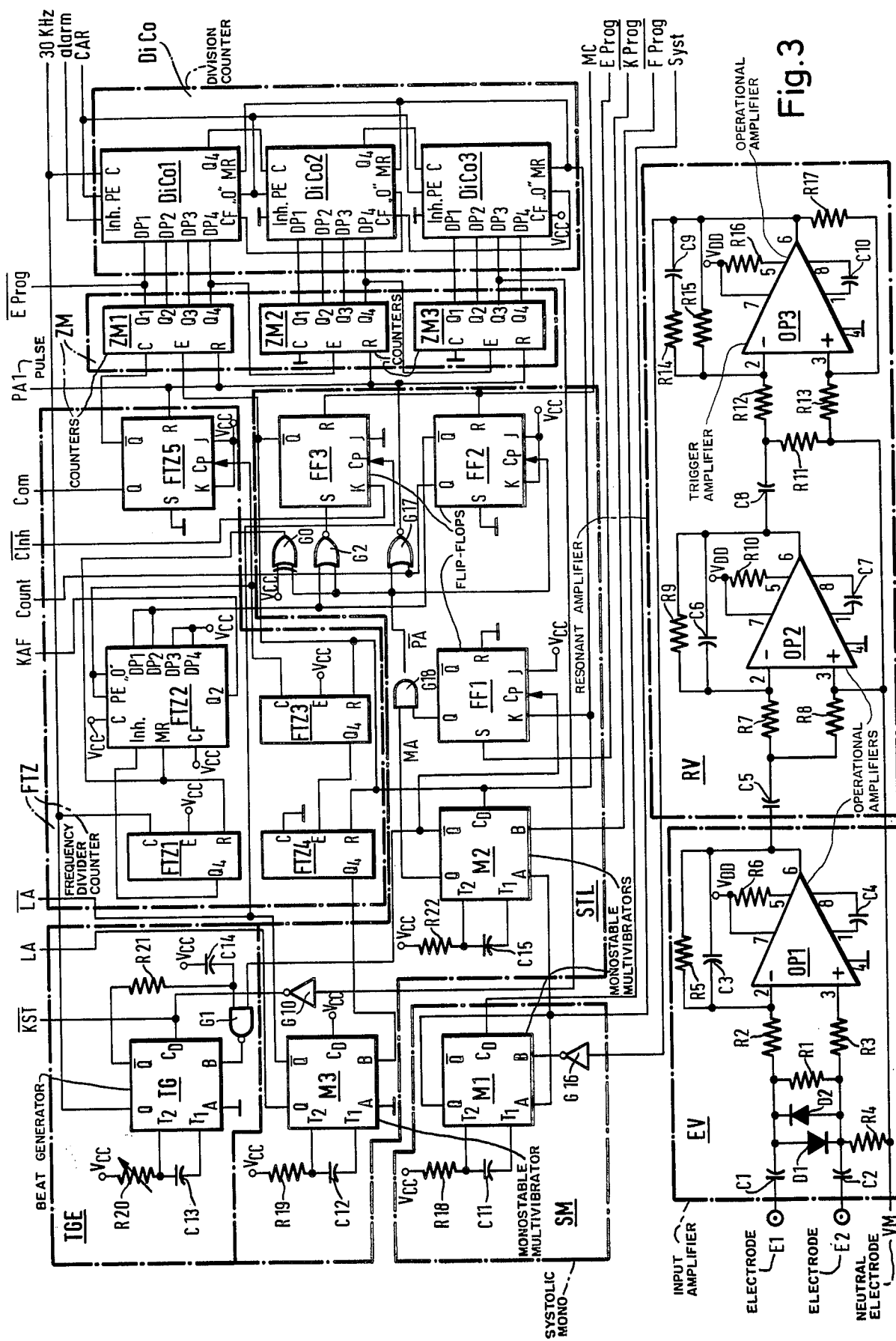
FIG. 3 shows the current pass of the input circuit of the digital circuit of the cardiac frequency measuring instrument in accordance with the invention.
Figure 4:
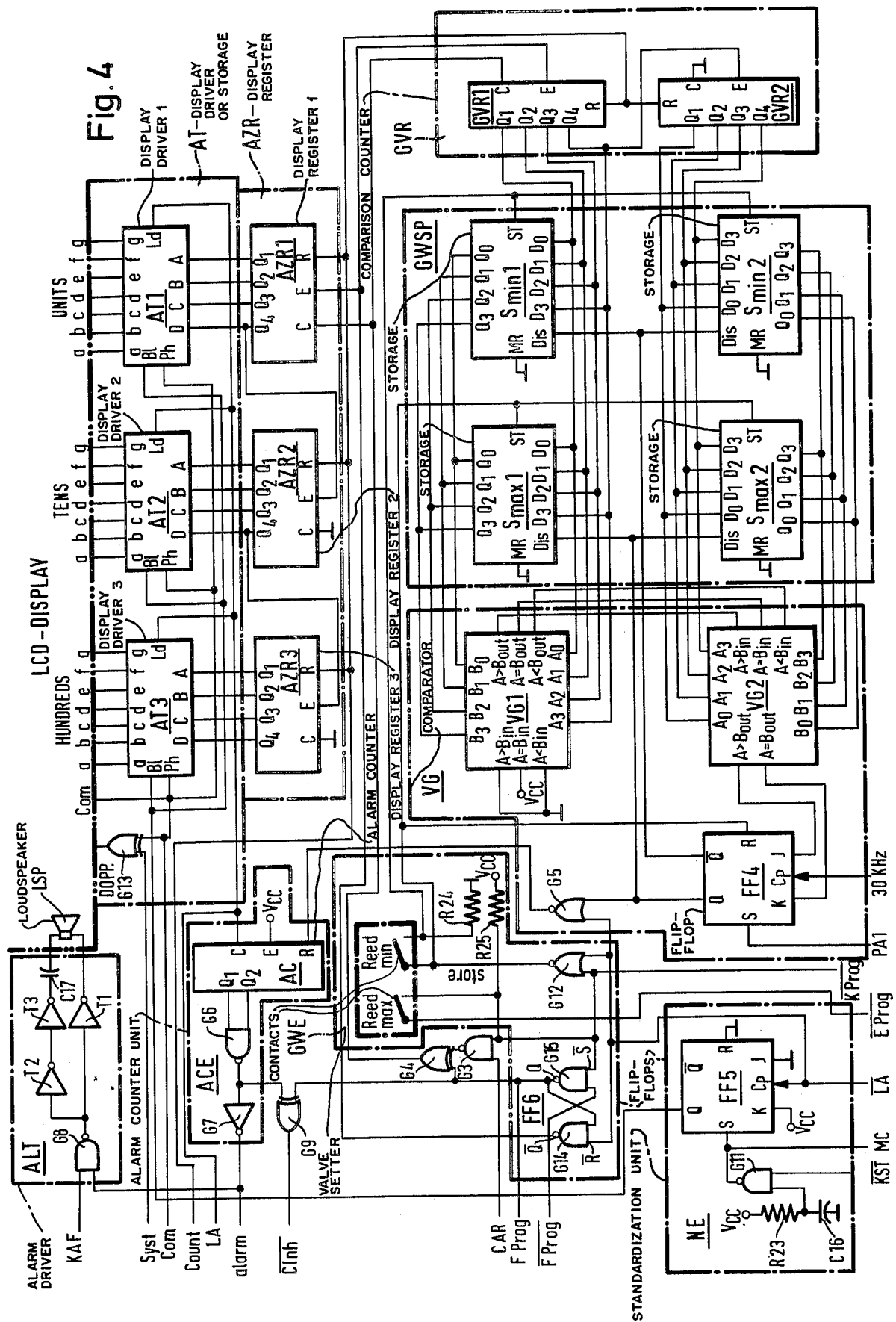
FIG. 4 shows a current pass of the storage and display circuit of the digital circuit of the cardiac frequency measuring instrument in accordance with the invention.

In what follows the construction of the circuitry with its various components will be described in detail with reference to the current circuits represented in FIGS. 3, 4 and 5.

DESCRIPTION OF THE CHIEF COMPONENTS USED IN THE CIRCUIT

The input circuit consists chiefly of three identical micropower operational amplifiers OP1, OP2 and OP3 coupled capacitively with each other and each of the type CA3078, which are differently connected and in the case of which the operational amplifier OP1 is connected as an input amplifier EV and the amplifier units OP2 and OP3 connected as resonant amplifiers or, respectively selective trigger amplifiers, together form the resonant amplifier stage RV. The rectangular signal produced in the input circuit consisting of the input amplifier EV and the resonant amplifier stage RV is supplied to the following logic circuitry via an inverter or buffer G16 of the type 4049.

The logic circuitry consists of several complexes, whose individual components are only explained briefly, while their precise connections are to be described later in the detailed description. The logic circuitry consists of several coherent complexes, that is to say chiefly of the systolic mono SM, the control logic STL, the frequency dividing counter FTZ, the clock unit TGE, the time measuring counter ZM, the division counter DiCo, the standardization unit NE, the comparison unit VGE, the limiting value storage GWSP, the limiting frequency comparison register GVR, the limiting value setter GWE, the display register AZR, the display driver AT, the alarm counter unit ACE and the alarm driver ALT.

The gates used in and between the individual complexes are conventional inverters, NAND gates, NOR gates and exclusive OR gates, which are preferably constructed in complementary MOS technology. The individual gates are denoted by references G0 to G18 and T1 to T3; in this respect the gates G1, G3, G6, G8, G11, G14, G15 and G18 are respectively NAND gates with two inputs (2-input NAND gates) of type 4011, the gates G2, G5, G12 and G17 are respectively NOR gates with two inputs (2-input NOR gates) of the type 4001, the gates G7, G10, G16, T1, T2 and T3 are respectively inverters or buffers of the type 4049 and the gates G0, G4, G9 and G13 are respectively exclusive OR gates with two inputs of type 4507.

The systolic mono SM consists essentially of the inverter G16 and the monoflop M1, while the control logic STL comprises the monoflops M2 and M3 and the flip-flops FF1, FF2 and FF3 and also the gates G0, G2, G10, G17 and G18. The frequency dividing counter FTZ comprises the five frequency dividing counting units FTZ1, FTZ2, FTZ3, FTZ4 and FTZ5, while the clock unit TGE consists chiefly of the monoflop TG as a beat generator or clock and the gate G1. The time measuring counter ZM comprises the three time measuring units ZM1, ZM2 and ZM3. The division counter DiCo also has three division counter units DiCo1, DiCo2 and DiCo3, while the standardizing unit NE comprises chiefly the flip-flop FF5 and the gate G11. The comparator VG consists of the two comparison units VG1 and VG2, the flip-flop FF4 and the gate G5. The limiting value storage GWSP is made up of the four storage units Smin1, Smin2, Smax1 and Smax2 and the two limiting frequency comparison register units GVR1 and GVR2 form the limiting value comparison register GVR. The limiting value setter GWE consists essentially of the two gates G14 and G15 making up the flip-flop FF6, the gate G12 and the two reed contacts Reedmax and Reedmin. The display register AZR consists of three identical indicating register units AZR1, AZR2 and AZR3, while the three identical display driver units AT1, AT2 and AT3 form the display driver AT. The alarm counter unit ACE consists of the alarm counter AC and the gates G6 and G7, while the alarm driver ALT for the loudspeaker LSP consists of the gates G8, T1, T2 and T3 and the capacitor C17.

The flip-flops FF1, FF2 and FF3 of the control logic STL, the flip-flop FF4 of the comparator VG, the flip-flop FF5 of the standardization unit NE and the frequency dividing counter FTZ5 are preferably in each case J-K flip-flops in complementary MOS-technology, each of the type 4027, in the case of which the J and K inputs, the CP clock input and the set and reset inputs R and S are respectively independent of each other. The two respective outputs of the flip-flops FF1 to FF5 and FTZ5 are as a matter of principle denoted as Q and $\bar{Q}$, in the case of which however it is not necessary for the two outputs to be connected in the case of all flip-flops employed and for example the Q output of the flip-flop FF3 and the respective $\bar{Q}$ outputs of FF1 and FF5 are not connected. The flip-flops FF1 to FF5 and FTZ5 operate respectively up to a typical toggle rate of 8 MHz with a minimum electrical power dissipation of approximately 50 nW.

The monoflop M1 of the systolic mono SM, the two monoflops M2 and M3 of the control logic STL and the beat generator TG of the clock unit TGE are preferably triggered monostable multi-vibrators (retriggerable, resettable monostable multivibrator) each of the type 4528. The connection of the inputs T1 and T2 with the capacitor and the resistor determines the pulse length of the monoflop. The respective clock inputs of the monoflops M1 to M3 and of the beat generator TG are denoted by CD and the respective two inputs are denoted by A and B, while two respectively separate outputs Q and $\bar{Q}$ are provided, which however do not necessarily have to be connected. For example the $\bar{Q}$ output of the monoflop M1 is not connected. All four monoflops M1, M2, M3 and TG can be triggered both by the front and also by the rear edge of an input pulse and produce a precise output pulse in a wide pulse length range, and the duration of the output pulses depends from the respective RC connection at the respective T1 and T2 inputs, that is to say of R20 and C13 in the case of the beat generator TG, of R19 and C12 in the case of the monoflop M3, of R18 and C11 in the case of the monoflop M1 and of R22 and C15 in the case of the monoflop M2.

The frequency dividing counter units FTZ1, FTZ3 and FTZ4 of the frequency dividing counter FTZ and the display register units AZR1 to AZR3 of the display register AZR are preferably constructed as four stage BCD counters or decade counters (4 stage BCD up counters) each of the type 4518 in complementary MOS-technology and are respectively provided with independent but mutually interchangeable C clock inputs and E enable inputs so that the respective counter can be caused to count up either with a positive or a negative pulse edge. Each of these counters FTZ1, FTZ3, FTZ4 and AZR1 to AZR3 can be cancelled by the application of a signal with a positive logic level at the R reset input; the respective four outputs are denoted by Q1 to Q4, of which naturally not all four outputs have to be connected. For example in the case of the frequency dividing counter units FTZ1, FTZ3 and FTZ4 only the respective Q4 output is connected.

With the selected connection of the frequency dividing counter units FTZ1, FTZ3 and FTZ4 using the respective Q4 outputs it is possible to ensure that these counters respectively divide by 10. The frequency dividing counter FTZ1 is in this respect set for division by 10 and this also applies for the frequency dividing counter FTZ3 and the frequency dividing counter FTZ4.

The respective Q1 to Q4 outputs of the display register units AZR1 to AZR3 are connected with the respective A to D inputs of the display driving units AT1 to AT3 and furthermore the Q4 output of the indicating register AZR1 is connected with the E enable input of the display register AZR2 and the Q4 output of the display register AZR2 is connected with the E enable input of the display register AZR3. With the selected connection of the display registers AZR1 to AZR3 and their connection together a cascading of the counting registers is made possible.

The frequency dividing counter unit FTZ2 of the frequency dividing counter FTZ and the three division counter units DiCo1, DiCo2 and DiCo3 of the division counter DiCo are respectively constructed as programmable binary counters (4 bit programmable divide-by-N-counters) respectively of the type 4526 in complementary MOS-technology and respectively have four inputs DP1 to DP4 and four outputs Q1 to Q4. These counters are counters which can be connected in the manner of a cascade and serve for counting down when respectively one decoded "0" output for events in the case of which division by N is carried out. The CF cascade feed-back input makes possible cascade-like events or operations without additional gates being necessary. These counters are furthermore respectively provided with a PE presetenable input and a MR master reset input, and the latter makes possible a synchronous beginning of the division cycle. Furthermore these counters are respectively provided with a C clock input and an Inh clock inhibit input, in the case of which the latter makes possible a switching off of the pulse counting function.

If a signal with a positive level is present at the respective Inh clock inhibit input of the division counter DiCo1 or, respectively, of the frequency dividing counter FTZ2, the respective counter is blocked and cannot count down. These counters employed for the division counters DiCo1 to DiCo3 and the frequency dividing counter FTZ2 can only count down again when the Inh input is converted to logical 0.

In the case of the connection selected for the frequency dividing counter FTZ2 the latter divides by 12 or 15 in accordance with the signal coming from the $\bar{Q}$ output of the flip-flop FF2 so that the frequency dividing counter FTZ2 in conjunction with the frequency dividing counter FTZ5 in one case provides a 200 Hz signal at its "0" output and in the other case provides 125 Hz for time measurement. The 200 Hz are required in order to obtain the 0.5 second for the computing cycle. In the case of an alarm cycle the frequency dividing counter FTZ2 provides at its Q2 output a signal of approximately 800 Hz.

The power requirement of these counters DiCo1 to DiCo3 and FTZ2, which operate with a counting frequency of 5 MHz, is 1 microwatt. In the case of these counters as well it is not necessary for all five outputs "0" and Q1 to Q4 to be connected and instead it is quite sufficient for the respective outputs required to be connected.

The time measuring counters ZM1, ZM2 and ZM3, the limiting frequency comparison registers GVR1 and GVR2 and the alarm counter AC are respectively constructed as four stage binary counters (4 stage binary up counter) respectively of the type 4520 in complementary MOS-technology and are provided with respectively separate but mutually interchangeable C clock inputs and E enable inputs so that these counters can be driven selectively with positive or negative pulse edge. Each of these counters can be cancelled by the application of a pulse with a positive level at the R reset input. Furthermore each of these binary counters has four outputs Q1 to Q4, of which, in a manner similar to the other counters previously explained, only the outputs required need to be connected. The power requirement of these counters operating up to a frequency of 6 MHz amounts to 1 microwatt for 6 MHz, something which is not achieved in the present case however.

The time measuring counters ZM1 to ZM3 and the limiting frequency comparison registers GVR1 and GVR2 are connected as conventional counters. The alarm counter AC also operates as a counter but however only the outputs Q1 and Q2 are connected. The alarm counter AC is connected via the line denoted by LA, via which the result of calculation is accepted in the display driver AT, with the monoflop M3, if it is not reset at zero in the case of the usual beat sequence three times in succession, it provides a respective positive signal at its two Q1 and Q2 outputs, with which in the present case via the gates G6 and G7 the signal "Alarm" is originated.

For the storage units Smin1, Smin2, Smax1 and Smax2 of the limiting value storge GWSP it is preferred to use 4 bit latches with a 3 state output each of the type 4508, whose four inputs are respectively referenced as D0 to D3 and whose four outputs are respectively referenced as Q0 to Q3. Each of these 4 bit latch units is provided with a ST strobe input and a MR master reset input and also with a Dis disable input, which are used as control inputs.

These storage units employed for the storages Smin1, Smin2, Smax1 and Smax2 only receive the data, present at the input, in the storage, if at the respective ST strobe control inputs of the respective storages a control signal with a positive level is present.

The two comparators VG1 and VG2 of the comparison unit VGE are respectively constructed as 4 bit comparators (4 bit magnitude comparator) of the type 4585 in complementary MOS-technology and have respectively eight comparison inputs A0 to A3 and B0 to B3, three cascade inputs "A $<$ B$_{in}$", "A $=$ B$_{in}$" and "A $>$ B$_{in}$" and three outputs "A $<$ B$_{out}$", "A $=$ B$_{out}$" and "A $>$ B$_{out}$". These comparators compare respectively two "words" A and B consisting respectively of 4 bits A0 to A3 and B0 to B3 with each other and determine whether they are smaller, equal or larger and after this comparison supply the correspondingly referenced output with a signal with a positive level. If "words" with more than 4 bits are to be compared with each other, such comparator units can be connected in tandem in a cascade-like manner by connecting the outputs referenced "A $<$ B", "A $=$ B" and "A $>$ B" of the first comparator with the correspondingly referenced inputs of the second comparator; the inputs referenced as "A greater than B" and "A less than B" of the first comparator are then connected with the lower level, the ground potential of the supply voltage, while the "A$=$B" input of the first comparator is connected with the upper level of the supply voltage. The comparators VG1 and VG2 also have a very low power consumption, which amounts to approximately 25 nW.

The three display driver elements AT1, AT2 and AT3 of the display driver AT are constructed respectively as BCD/7 segment latch decoder driver stages for liquid crystal display systems (BCD to 7 segment latch decoder driver for liquid crystals) each of the type 4543 in complementary MOS-technology, and these display drivers respectively perform the functions of a 4 bit storage latch and a BCD/7 segment decoder and driver. The four respective inputs denoted with A to D are conveniently connected with the corresponding outputs of a register, while the respective seven outputs $a$ to $g$ are respectively connected with the corresponding seven segments of a liquid crystal or LCD display.

Furthermore the driver elements AT1 to AT3 are provided with a Ph-phase input for conversion of the truth table phase, a B1 blanking input for blanking the display and a Ld load input for storing a BCD code. For liquid crystal (LCD) displays a rectangular alternating voltage signal is applied at the Ph-phase input of the respective display driver and at the common backplate of the display element; in the present case the signal "Com" is used with a frequency of 125 Hz and, respectively 100 Hz.

The respective seven outputs $a$ to $g$ of the display driver AT1 to AT3 are connected directly with the seven segments of the LCD display, which for example are arranged in the form of a stylised "8" consisting of seven lines, with two squares arranged one above the other and one shared side. By driving the respective segments of the seven "lines" the numbers 0 to 9 can be directly displayed. The display driver AT1 to AT3 can however be also used jointly with other display units, for example with LED's with incandescent displays, gas discharge displays or fluorescent displays or the like, in which case specific display driver elements will have to be used which are suitably connected.

CONSTRUCTION OF THE CIRCUITRY

The input circuit of the circuitry chiefly consists of a three stage amplifier with three operational amplifiers OP1, OP2 and OP3 connected in tandem or cascade, which form an input amplifier EV and a resonant amplifier RV connected with it. The connections denoted by references 1 to 8 of the three operational amplifiers OP1, OP2 and OP3 are the conventional eight connections and the inverting and non-inverting inputs are referenced as 2 and 3 respectively, the inputs for frequency compensation are referenced with 1 and 8, the positive supply is referenced with 7, the negative supply is referenced with 4, the biasing voltage input is referenced with 5 and the output is referenced with 6.

Figures 5, 6:
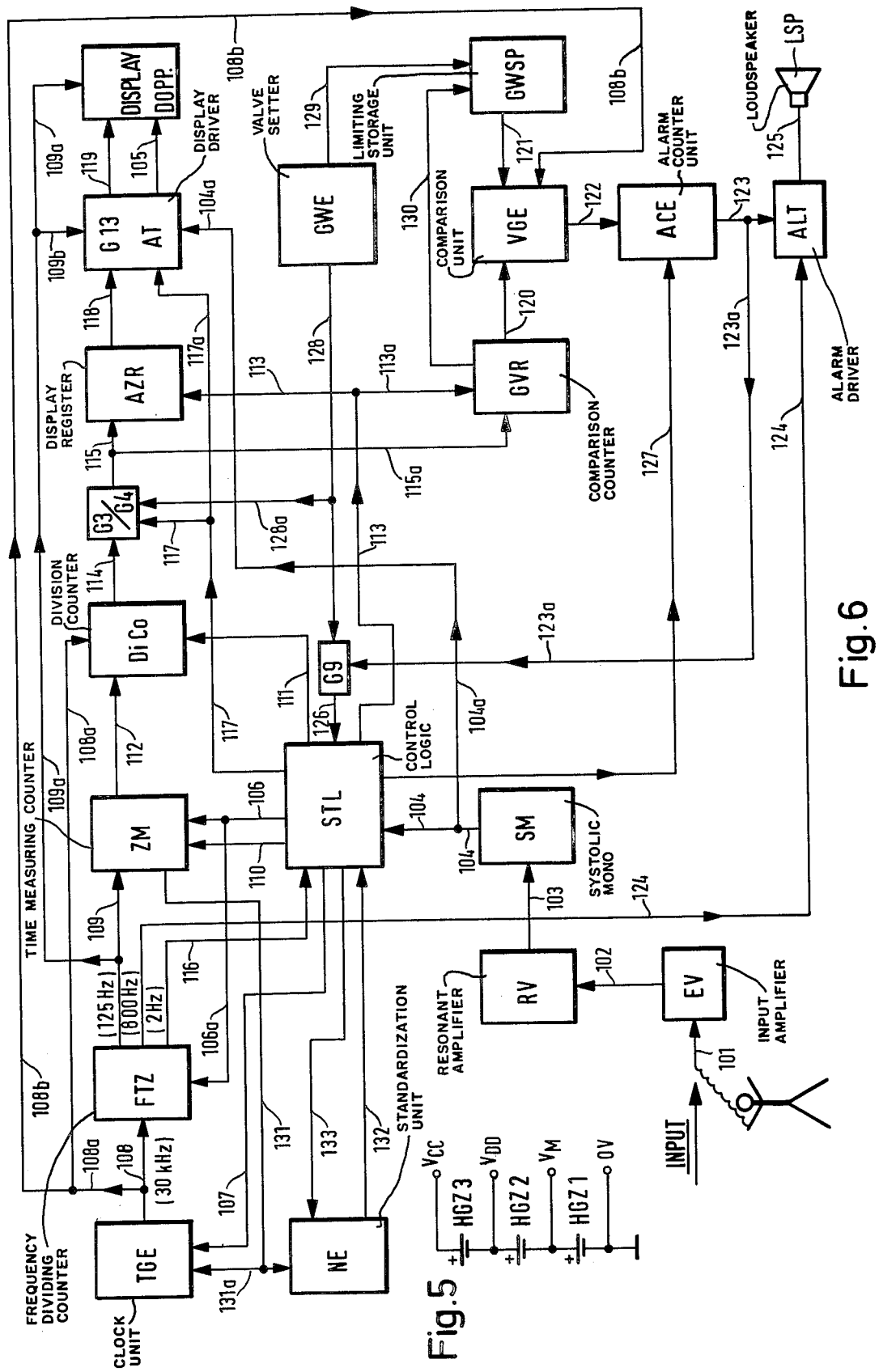
FIG. 5 shows a circuit of the voltage supply system for the circuits in accordance with FIGS. 3 and 4.
FIG. 6 is a block circuit diagram for explaining the manner of operation of the digital circuit shown in FIGS. 3 to 5, of the cardiac frequency measuring instrument in accordance with the invention.

The different supply voltages and potentials used in the circuits are indicated in FIG. 5. In this figure three identical mercury cells HGZ1, HGZ2 and HGZ3 are connected in series. In the case of a first embodiment these mercury cells respectively supply a voltage of 1.2 so that the neutral electrode VM has a potential difference of 1.2 V with respect to the zero or ground potential, while the supply voltages VDD and VCC exhibit a potential difference of 2.4 V and, respectively, 3.6 V with respect to the ground potential.

In the case of another preferred embodiment the mercury cells HGZ1 to HGZ3 respectively provide a voltage of 1.35 so that the neutral electrode VM exhibits a potential difference of 1.35 V with respect to the ground potential, while the supply voltages VDD and VCC in this case exhibit a potential difference of 2.7 V and, respectively, 4.05 V with respect to ground potential. In the two cases in the circuitry the supply voltage VDD is preferably used for the three operational amplifiers OP1, OP2 and OP3, while the other components employed in the circuitry, which require a supply voltage, operate with the supply voltage VCC.

An ECG signal, sensed via two stick-on electrodes E1 and E2 on the thorax, amounting to approximately 1 mV is coupled via two coupling capacitors C1 and C2 of equal size capacitively with the input circuit of the operational amplifier OP1 to identical diodes D1 and D2 connected antiparallel between C1 and C2 and the inputs 2 and 3 of the operational amplifier OP1 prevent damage to the difference inputs 2 and 3 of the operational amplifier OP1 by high static voltages, since they become conducting at a voltage of 0.7 V and thus do not allow the voltage to rise any further. The resistor R1 connected in parallel to the diodes D1 and D2 between the two capacitors C1 and C2 forms the termination within the input current circuit. The resistor R4 between the capacitor C2 and the resistor R3 connected with the input of OP1 on the one hand and the neutral electrode VM on the other hand ensures that the input circuit maintains a definite zero potential at all times with respect to the two inputs 2 and 3 of the operational amplifier OP1. The resistor R2, between the capacitor C1 and the input 2 of OP1, and the resistor R5 between the input 2 and the output 6 of the operational amplifier OP1, bring about a defined amplification of the input signal by a factor 150.

The capacitor C3 connected in parallel with the resistor R5 ensures, providing capacitative negative feedback, that high frequencies passing via the input circuit into the amplifier circuit are not amplified.

The resistor R3 between the capacitor C2 and the input 3 of OP1 has for reasons of symmetry the same value as the resistor R2. The supply voltage VDD is directly supplied to the positive supply input 7 and via the resistor R6 to the supply input 5 of OP1, and the value of the resistor R6 influences the resting or quiescent current of OP1 and the maximum rise speed of the output signal. The resistor R6 is so selected that the smallest possible supply current for the operational amplifier OP1 is required and nevertheless in every case the necessary rise time for the QRS complex of the ECG signal with 16 Hz is guaranteed. Between the compensation inputs 1 and 8 of OP1 there is a capacitor C4 for external frequency compensation, while the negative supply input 4 of OP1 is placed at ground potential.

The resonant amplifier, consisting of the two operational amplifiers OP2 and OP3, is coupled via a capacitor C5 with the output 6 of OP1, which couples in the complete and undistorted ECG signal to the resonant amplifier OP2, which is connected via the resistor R7 with the inverting input 2 and via the resistor R8 (of the same size for symmetry reasons) connected in parallel to R7 is connected with the non-inverting input 3 of the operational amplifier OP2. The input 3 of OP2 is furthermore directly connected with the neutral electrode VM. The supply voltage VDD is connected directly with the positive supply input 7 and is connected via a resistor R10 with the supply input 5 of OP2, while between the compensation inputs 1 and 8 of OP2 a capacitor C7 is connected for external frequency compensation; the negative supply input 4 is placed at ground potential.

Between the inverting input 2 and the output 6 of OP2 a resistor R9 is connected and in parallel to it a capacitor C6 is connected. In the case of this resonant amplifier OP2, connected as a passive high pass filter for frequencies above approximately 16 Hz, the capacitor C5 and the resistor R8 limit the frequency range downwards, while the capacitor C6 and the resistor R7 limit the frequency range upwards. The resistors R7 and R9 determine the amplification of the operational amplifier OP2, while the negative feed back capacitor C6 again serves for suppressing any high speed pulses coming as far as this amplifier. The resistor R10 of OP2 determines in a manner similar to the resistor R of OP1 the quiescent current and the voltage rise speed of the operational amplifier. The connection of the operational amplifier OP2 is so selected that by determining the lower limiting frequency at approximately 16 Hz pulses of slow movements as for example the so-called T wave of the final variation of the ECG or movement artefacts, can pass the amplifier OP2 connected as a high pass filter, if anything only in an attenuated form.

The output signal present at the output 6 of OP2 is coupled in via a capacitor C8 into an operational amplifier OP3 connected as an selective trigger amplifier and is applied via the resistor R12 to the inverting input 2 and the resistors R11 and R13 connected in parallel to R12 are connected with the non-inverting input 3 of OP3. Furthermore the non-inverting input 3 of OP3 is connected via the resistor R13 with the neutral electrode VM. Between the frequency compensation inputs 1 and 8 of OP3 a capacitor C10 is connected for external frequency compensation, while the negative supply input 4 of OP3 is connected with the ground potential. The supply voltage VDD is connected directly with the positive supply input 7 and via the resistor R16 is connected with the biasing voltage input 5 of OP3. Between the input 2 and the output 6 of OP3 a resistor R15 is connected and in parallel to it there is a resistor R14. In series with R14 there is a capacitor C9. The input 3 of OP3 is connected via a resistor R17 with the output 6 of OP3.

The coupling capacitor C8 and the resistor R11 again in turn form a passive high pass filter for frequencies above approximately 16 Hz so that low frequencies due to movement artefacts, muscle artefacts or the like are attenuated. The resistors R12 and R15 determine the amplification of the trigger amplifier OP3 while high speed pulses are suppressed via the resistor R14 and the capacitor C9 in the amplifier circuit. The value of the resistor R16 determines the quiescent current and the voltage rise time of OP3, in the case of which a somewhat higher quiescent current must be put up with as compared with the amplifiers OP1 and OP2 in order to obtain the best possible rectangular output signal. If the output 6 of the operational amplifier OP3 reaches the trigger level determined by the resistors R13 and R17, via the positive input 3 of OP3 a coupling or positive feed back effect is obtained, which ensures that the output pulse present at the output 6 of the trigger amplifier OP3 becomes a rectangle.

The rectangular output signal present at the output 5 of the trigger amplifier OP3 is the output signal of the whole input circuit, which is coupled via an inverter G16 via the B input of the monoflop M1 into the systolic mono SM. The monoflop M1 is, just like the monoflops M2 and M3, and the clock TG, a monostable multivibrator which can be triggered and reset. The supply voltage VCC of the monoflop M1 is applied via a resistor R18 at the input T2 and is applied via a capacitor C11, connected in series with the resistor R18, at the input T1. In a similar manner the supply voltage VCC in the case of the monoflop M2 is applied via a resistor R22 at the input T2 and it is applied via a capacitor C15, connected in series with the resistor R22, with the input T1 of the monoflop M2 so that the inputs T1 and T2 are respectively capacitatively separated and the RC combinations, connected with the T1 and T2 inputs, determine the pulse length of the monoflops.

The Q output of the monoflop M1 is connected both at its own A input, in order to prevent retriggering, and also at the A input of the monoflop M2 and however also via the line denoted with Syst with an input of the exclusive OR gate G13, something which makes possible a flashing display of the double point. If the monoflop M1 is started, simultaneously the monoflop M2 starts, which is connected at its $\overline{Q}$ output with the one input of the NAND gate G1 and via the gate G1 starts the clock TG via its B input. The other input of the NAND gate G1 is connected via a capacitor C14 with the supply voltage VCC and is connected in parallel to the capacitor C14 via a resistor R21 with the $\overline{Q}$ output of the clock TG. The clock TG is a monostable multivibrator of the same type as the monoflops M1, M2 and M3, which has its input T2 connected via an adjustable resistor R20 with the supply voltage VCC and its input T1 is connected via the capacitor C13 and the resistor R20 connected in parallel with the supply voltage VCC and the RC combination at the inputs T1 and T2 determines the pulse length of the clock TG. The A input of the beat generator TG lies at ground potential.

The $\overline{Q}$ output of the monoflop M2 is furthermore connected with the clock input CP of the J-K flip-flop FF1 so that on starting the monoflop M2 the settable and resettable flip-flop FF1 is set. The J input of the flip-flop FF1 is connected directly with the supply voltage VCC, while the K input of the flip-flop FF1 is connected with the trigger input CD of the monoflop M2, with the R trigger inputs of the frequency dividing counters FTZ3 and FTZ4, with the Q output of the J-K flip-flop FF3 and with the E enable input of the time measurement counter ZM1. The S set input of the flip-flop FF1 is connected via the line referenced FProg, with the Q output of the flip-flop FF6 consisting of the NAND gates G14 and G15, and with respectively one input of the two exclusive OR gates G4 and G9, connected in this manner with each other, while the R reset input of the flip-flop FF1 is at ground potential. The $\overline{Q}$ output of the flip-flop FF1 is, just like the $\overline{Q}$ output of the monoflop M1, not connected. The Q output of the flip-flop FF1 is connected with one input of the NAND gate G18, whose other input is connected with the Q output of the monoflop M2. The output of the NAND gate G18 is connected respectively with one input of the NOR gates G17 and G2 and of the exclusive OR gate G0 and with the CP clock input of the J-K flip-flop FF2. The J input and the K input of the settable and resettable flip-flop FF2 are connected both directly with the supply voltage VCC; its S set input lies at ground potential and its R reset input is connected with the R reset input of the J-K flip-flop FF3 and via the line referenced MC with the S set input of the J-K flip-flop FF5 and is connected with the output of the NAND gate G11, which accordingly can drive the S input of FF5 and the R inputs of FF2 and, respectively, FF3.

The Q output of the flip-flop FF2 is connected with the second input of the NOR gate G17 and is furthermore connected via the line, denoted Count with the respective R reset inputs of the display registers AZR1 to AZR3 and the respective R reset inputs of the limiting frequency comparison registers GVR1 and GVR2. The Q output of the flip-flop FF2 is connected with the second input of the NOR gate G2 and at the two inputs DP1 and DP2 of the frequency dividing counter FTZ2. The NOR gate G17 connected with the $\overline{Q}$ output of the flip-flop FF2 and the output of the gate G18 has its output connected with the respective R reset inputs of the time measuring counters ZM1 to ZM3, with the reset input of the frequency dividing counter FTZ5 and via the line, referenced PA1, with the S set inputs of the J-K flip-flop FF4.

The NOR gate G2 connected with the Q output of the flip-flop FF2 and with the output of the NAND gate G18 has its output connected with the S set input of the J-K flip-flop FF3 and can set the latter. The exclusive OR gate G0 has its one input connected with the output of the NAND gate G18 and has its second input connected with the supply voltage VCC, while its output is connected with the MR master reset input of the frequency dividing counter FTZ2 and the R reset input of the frequency dividing counter FTZ1. The frequency dividing counters FTZ1, FTZ3 and FTZ4 are respectively four stage BCD counters (BCD up counters). The frequency dividing counter FTZ2 is a programmable binary 4-bit counter (programmable divide-by-N 4-bit counter) and the frequency dividing counter FTZ5 is a settable and resettable J-K flip-flop. The individual frequency dividing counters FTZ1 to FTZ5 form the whole frequency dividing counter FTZ.

The frequency dividing counter FTZ1 has its E enable input connected with the supply voltage VCC, while its C clock input is connected with the Q output of the clock TG. The Q output of the clock TG is furthermore connected with the C clock input of the division counter DiCo1 and the CP clock input of the J-K flip-flop FF4. The Q4 output of the frequency dividing counter FTZ1 is connected with the Inh count inhibit input of the frequency dividing counter FTZ2. The DP3 and DP4 inputs, the CF count feed-back input and the C clock input of the frequency dividing counter FTZ2 are connected directly with the supply voltage VCC. The "O" output of the frequency dividing counter FTZ2 is connected directly with the PE presettable input of FTZ2, with the CP clock input of the frequency dividing counter FTZ5 and with the C clock input of the frequency dividing counter FTZ3. The Q2 output of the frequency dividing counter FTZ2 is connected via the line referenced KAF with one input of the NAND gate G8 of the alarm driver ALT.

The E enable input of the frequency dividing counter FTZ3 is directly connected with the supply voltage VCC while the Q4 output of FTZ3 is connected with the E enable input of the frequency dividing counter FTZ4. The C clock input of FTZ4 is placed at ground potential, while its Q4 output is connected with the B input of the monoflop M3. The A input of the monoflop M3 lies at ground potential. The monoflop M3 is connected at its input T2 via a resistor R19 with the supply voltage VCC and its input T1 is connected via a capacitor C12, connected in series with the resistor R19, with the supply voltage VCC and the RC combination at the inputs T1 and T2 determines the pulse length of the monoflop M3. The Q output of the monoflop M3 is connected via the line referenced LA with the C clock input of the alarm counter AC constructed as a four stage binary counter, and is connected with all Ld load inputs of the three display drivers AT1 to AT3. The $\overline{Q}$ output of the monoflop M3 is connected on the one hand with the CP clock input of the flip flop FF3 and on the other hand is connected via the line referenced $\overline{LA}$ with the CP clock input of the flip-flop FF5 and there is also a connection with one input of the NOR gate G5 and G12 and the $\overline{R}$ input of the gate G14 of the flip-flop FF6.

The J and K inputs of the frequency dividing counter FTZ5 are directly connected with the supply voltage VCC; its S set input is connected with ground potential. The Q output of the frequency dividing counter FTZ5 is connected via the line referenced Com with the second input of the exclusive OR gate G13 for controlling or driving the flashing double point DOPP and with the so-called common plate connection of the LCD display and it is furthermore connected with all Ph-phase inputs of the display drivers AT1 to AT3. The $\overline{Q}$ output of the frequency dividing counter FTZ5 is connected with the C clock input of the time measuring counter ZM1. The Q1 to Q4 outputs of the time measuring counter ZM1 are connected with the DP1 to DP4 inputs, indexed in the same manner, of the division counter DiCo1, Q1 being connected with DP1 and so on until Q4 is connected with DP4. The output Q1 of the time measuring counter ZM1 is furthermore connected via the line referenced $\overline{EProg}$ with the reed contact Reedmax of the limiting value setter GWE, while the Q4 output of the time measuring counter ZM1 is connected with the E enable input of the time measuring counter ZM2. The respective C clock inputs of the time measuring counters ZM2 and ZM3 are both connected with ground potential. The respective outputs Q1 to Q4 of the time measuring counter ZM2 are in turn connected with the respective inputs DP1 to DP4 of the division counter DiCo2 in the sequence Q1 with DP1,..., Q4 with DP4. The Q4 output of the time measuring counter ZM2 is furthermore connected with the E enable input of the time measuring counter ZM3 and the respective Q1 to Q4 outputs of the time measuring counter ZM3 and in turn connected with the respective inputs DP1 to DP4 of the division counter DiCo3, Q1 being connected with DP1,..., Q4 with DP4. Furthermore the Q3 output of the time measuring counter ZM3 is connected via the inverter G10 with the CD clock input of the clock TG and furthermore it is connected via the inverter G10 and the line denoted $\overline{KST}$ with one input of the NAND gate G11.

The "O" output of the division counter DiCo1 is connected with all PE presetenable inputs of the three division counters DiCo1 to DiCo3, while the "O" output of the division counter DiCo2 is connected with the CF cascade feed-back input of the division counter DiCo1 and the "O" output of the division counter DiCo3 is connected with the CF cascade feed-back input of the division counter DiCo2. The CF cascade feed-back input of the division counter DiCo3 is connected directly with the supply voltage VCC. The Inh clock inhibit inputs of the division counters DiCo2 and DiCo3 are connected with ground potential. All MR master reset inputs of the three division counter DiCo1 to DiCo3 are connected with the $\overline{Q}$ output of the flip-flop FF3. The Q4 output of the division counter DiCo1 is connected with the C clock input of the division counter DiCo2 and its Q4 output is connected with the C clock input of the division counter DiCo3.

The J-K flip-flop FF5 of the standardising unit NE has its CP clock input connected with the $\overline{Q}$ output of the flip-flop M3 via the line referenced $\overline{LA}$. The J input and also the R reset input of the flip-flop FF5 are connected with ground potential. The K input is directly connected with the supply voltage VCC. The gate G11 has its one input connected via the inverter G10 with the Q3 output of the time measuring counter ZM3, while the second input of the NAND gate G11 is connected via a resistor R23 with the supply voltage VCC and via a capacitor C16 is put off from ground potential. The output signal of the NAND gate G11 is applied to the S set input of the flip-flop FF5 and via the line referenced MC with the R reset inputs of the two flip-flops FF2 and FF3. The Q output of the flip-flop FF5 is connected with the respective B1 blanking inputs of the three display drivers AT1 to AT3.

While the one pole of the reed contact Reedmax is connected via the line $\overline{EProg}$ with the Q1 output of the time measuring counter ZM1, the second pole of the reed contact Reedmax is connected respectively with one input of the NAND gate G3, with the $\overline{S}$ input of the NAND gate G15 of the flip-flop FF6 and with the second input of the NOR gate G12, whose first input is connected via the line $\overline{LA}$ with the $\overline{Q}$ output of the flip-flop M3. Additionally the line referenced $\overline{KProg}$ is connected with the B input of the monoflop M2; this line is continued when the Reedmax is not closed via the resistor R25 to VCC. The output of the NOR gate G12 is connected with one pole of the reed contact Reedmin, with the R reset input of the flip-flop FF4 and the respective ST strobe inputs of the storage Smax1 and Smax2. The second pole of the reed contact Reedmin is directly connected with the respective ST strobe inputs of the two storages Smin1 and Smin2 and when Reedmin is not closed is connected with the ground potential via the resistor R24, that is to say it has the value of logical 0.

The flip-flop FF6 of the limiting value setter GWE consists of the two NAND gates G14 and G15. The $\overline{R}$ input of the gate G14 is connected via the line $\overline{LA}$ with the $\overline{Q}$ output of the monoflop M3 and its second input is connected with the Q output of the NAND gate G15. The $\overline{S}$ input of the NAND gate G15 is connected via the resistor R25 with the supply voltage VCC and when the reed contact Reedmax is closed it is connected via the line $\overline{EProg}$ with the Q1 output of the time measuring counter ZM1, while its second input is connected with the $\overline{Q}$ output of the gate G14. The Q output of the gate G15 is connected via the line referenced FProg with the S set input of the flip-flop FF1, while the CD clock input of the monoflop M1 is connected with the line referenced $\overline{FProg}$ with the $\overline{Q}$ output of the gate G14 of the flip-flop FF6. The one input of the NAND gate G3 is connected with the second pole of the reed contact Reedmax and via the resistor R25 with the supply voltage VCC; the second input of the NAND gate G3 is connected via the line referenced CAR with the "O" output of the division counter DiCo1. The output of the NAND gate G3 is connected with the one input of the exclusive OR gate G4, while the other input of the gate G4 is connected with the Q output of the gate G5 of the flip-flop FF6 and is connected with one input of the exclusive OR gate G9. The output of the exclusive OR gate G4 is connected with the C clock input of the display register AZR1 and with the C clock input of the limiting frequency comparison register GVR1. The E enable input of the limiting frequency comparison register GVR1 and the E enable input of the display register AZR1 are connected with each other and are both connected with the $\overline{Q}$ output of the NAND gate G14 of the flip-flop FF6.

The inputs A0 to A3 of the comparator VG1 and the respective identically indexed inputs D0 to D3 of the two storages Smin1 and Smax2 are respectively connected together and are connected with the outputs Q1 to Q4 of the limiting frequency comparison register GVR1. The output Q1 is connected with the respective inputs D0 and A0 indexed 0. The output Q2 is connected with the respective inputs D1 and A1 indexed 1. The output Q3 is connected respectively with the inputs D2 and A2 indexed 2 and the output Q4 is connected respectively with the inputs D3 and A3 indexed 3. The output Q4 of the limiting frequency comparison register GVR1 is furthermore connected with the E enable input of the limiting frequency comparison register GVR2, while the C clock input of GVR2 is at ground potential. All MR master reset inputs of the four storages Smin1, Smin2, Smax1 and Smax2 are at ground potential. The four outputs Q0 to Q3 of the storage Smin1 are connected with the four outputs Q0 to Q3 of the storage Smax1 and in a manner parallel to this are connected with the four inputs B0 to B3 of the comparator VG1 so that the respective connections with the same indices 0, 1, 2 and 3 are connected with each other.

The four outputs Q1 to Q4 of the limiting frequency comparison register GVR2 are connected with the four inputs D0 to D3 of the storage Smin2, the four inputs D0 to D3 of the storage Smax2 and the four inputs A0 to A3 of the comparator VG2 so that the inputs respectively indexed with 0 are connected with the Q1 output, the inputs indexed with 1 are connected with the Q2 output, the inputs indexed with 2 are connected with the Q3 output and the inputs indexed with 3 are connected with the Q4 output. Furthermore all D inputs with the same indices of the storages Smin2 and Smax2 are connected with each other and in parallel to this with the A inputs having the same indices of the comparator VG2. The outputs Q0 to Q3 of the storage Smin2 are respectively connected with the outputs Q0 to Q3 of the storage Smax2 and with the inputs B0 to B3 of the comparator VG2 in the case of which the Q outputs with respectively the same indices of the two storages Smin2 and Smax2 are connected with each other and in parallel to this with the inputs having the same indices of the comparator VG2.

The "A > $B_{in}$" input and the "A < $B_{in}$" input of the comparator VG1 are at ground potential, while the "A = $B_{in}$" input of the comparator VG1 is connected directly with the supply voltage VCC. The comparator VG1 and the comparator VG2 are so connected with each other that the "A > $B_{out}$" output of VG1 is connected with the "A > $B_{in}$" input of VG2, the "A = $B_{out}$" output of VG1 is connected with the "A = $B_{in}$" input of VG2 and the "A < $B_{out}$" output of VG1 is connected with the "A < $B_{in}$" input of VG2. The "A > $B_{out}$" output of the comparator VG2 is connected with the J input of the J-K flip-flop FF4 and the "A = $B_{out}$" output of the comparator VG2 is connected with the K input of the flip-flop FF4. The Q output of the flip-flop FF4 is connected with the respective Dis disable inputs of the two storages Smin1 and Smin2. The $\overline{Q}$ output of the flip-flop FF4 is connected with the respective Dis disable inputs of the two storages Smax1 and Smax2 is furthermore connected with one input of the NOR gate G5, whose other input is connected via the line $\overline{LA}$ with the Q output of the monoflop M3.

The output of the NOR gate G5 is connected with the R reset input of the alarm counter AC, while its E enable input is connected directly with the supply voltage VCC.

The two outputs Q1 and Q2 of the alarm counter AC are connected with the two inputs of the NAND gate G6. The output of the NAND gate G6 is connected with the input of the inverter G7 on the one hand and on the other hand it is connected with one input of the exclusive OR gate G9, whose other input is connected with the Q output of the NAND gate G15 of the flip-flop FF6. The output of the exclusive OR gate G9 is connected via the line referenced $\overline{CInh}$ with the K input of the flip-flop FF3; the J input of the flip-flop FF3 is at ground potential.

The signal inverted in the inverter G7 of the NAND gate G6 on the one hand is applied to the Inh clock inhibit input of the division counter DiCo1 via the line referenced alarm and on the other hand it is connected with one input of the NAND gate G8, which has its other input connected via the line KAF with the Q2 output of the frequency dividing counter FTZ2. The output of the NAND gate G8 of the alarm driver ALT is connected on the one hand via the inverting driver T1 with one pole of the loudspeaker LSP and on the other hand it is connected via the drivers T2 and T3, connected in series, and the following capacitor C17 with the other pole of the loudspeaker LSP. The loudspeaker LSP is preferably a directional loudspeaker, whose audio frequency has a value of approximately 800 Hz.

The display register AZR consists of three display register units AZR1 to AZR3, whose R reset inputs are respectively connected via the line Count with the Q output of the flip-flop FF2. Furthermore the display register AZR1 has its E enable input connected with the $\overline{Q}$ output of the gate G14 of the flip-flop FF6 while by means of its C clock input it is connected with the output of the exclusive OR gate G4. The individual display driving units AT1 to AT3 are connected with the respective display register units AZR1 to AZR3 in such a manner that the respective outputs Q1 to Q4 of the display register units are connected with the respective inputs A to D of the display driver units, that is to say in each case Q1 is connected with A, Q2 is connected with B, Q3 is connected with C and Q4 is connected with D. Furthermore the Q4 output of the display register AZR1 is connected with the E enable input of the display register AZR2 and the Q4 output of the display register AZR2 is connected with the E enable input of the display register AZR3. The respective C clock inputs of the two display registers AZR2 and AZR3 are respectively connected with ground potential.

The respective seven outputs a to g of the three display driver units AT1 to AT3 are connected with the respective seven segments of the three LCD display units for display of the ones, tens and hundreds digits and the seven segments of the display are for example seven lines, which are arranged in the form of squares placed one above the other with one joint side and form a stylised "8". By respective driving of the respective outputs a to g the respective numbers 0 to 9 can be displayed at the respective positions. Naturally instead of LCD display elements it is possible to use other display elements as for example LED's or the like, if they have a suitably low power requirement and the batteries are not more loaded by them than is the case with the LCD display. In the case of the use of other display elements it is naturally necessary to use suitable types of display driving elements to be connected.

THE BLOCK CIRCUIT DIAGRAM

For explaining the general manner of operation of the circuit in what follows the block circuit diagram is to be explained with reference to FIG. 6. In this respect the term "line" is to be taken to mean the wider context of a "signal path" so that as regards the detailed current passage this is partly to be understood as a reference to individual conductors and partly bundles of conductors.

Via the line 101 the ECG signal of the patient passes with a level of approximately 1mV to the input amplifier EV, which amplifies the input signal to a level of approximately 100 mV and supplies it via the line 102 to the resonant amplifier RV. The resonant amplifier RV selects from the ECG signal the QRS complex and converts this signal into a rectangular or square pulse, which passes along the line 103 in order to actuate the monoflop M1 of the systolic mono SM.

The monoflop M1 of the systolic mono SM for its part drives by means of the signal "Syst" via the line 104a and the exclusive OR gate G13 in the display driver AT and via the line 105 the double point DOPP in the display. Furthermore, the monoflop M1 of the systolic mono SM drives via the line 104 the control logic STL; in the control logic STL the signals MA, $\overline{PA}$ and PA1 are produced, with which the control logic via the line 106 standardizes or sets the time measuring counter ZM and, respectively, via the line 106a sets the frequency dividing counter FTZ and furthermore via the line 107 starts the beat generator or clock TG of the clock unit TGE.

The clock TG of the clock unit TGE controls with its output with a 30 kHz clock via the line 108 the frequency dividing counter FTZ and via the line 108a controls the division counter DiCo and via the line 108b controls the flip-flop FF4 of the comparison unit VGE. The frequency dividing counter FTZ produces now a 125 Hz clock, which causes via the line 109 the time measuring counter ZM to count; this 125 Hz clock of the frequency dividing counter FTZ is furthermore applied as a signal "Com" via the lines 109a and 109b at the display driver AT and, respectively, at the display and at this position produces the A.C. required for the LCD display.

If the control logic STL recognizes the third QRS complex arriving via the lines 101, 102, 103 and 104, the control logic STL stops while producing the signals MA, $\overline{PA}$ and PA1 via the line 110 the time measuring counter ZM and enables via the line 111 the division counter DiCo for processing the data arriving via the line 112 from the time measuring counter ZM. The display registers AZR and, respectively the limiting frequency comparison registers GVR held at 0 by the control logic STL with the signal "Count" via the lines 113 and, respectively, 113a during the whole time measuring cycle are now enabled and the result pulses of the division counter DiCo can with the signal "CAR" via the line 114, the two gates G3 and G4 and the lines 115 and 115a, count up the display register AZR and, respectively the limiting frequency comparison register GVR.

At the end of such a division, which is signalled by the frequency dividing counter FTZ with a signal in a 2 Hz clock via the line 116 to the control logic STL, the result presented via the line 118 to the display driver AT, of the display register AZR is transferred to the display driver AT, since the control logic STL via the line 117 and, respectively, 117a controls with the control signal "LA" the gates G3 and G4 and respectively the display driver AT. Via the line 119 the display data of the display driver AT is presented to the LCD segments and displayed by them.

The data built up during the division in the limiting frequency comparison register GVR is investigated via the line 120 by the comparison unit VGE as regards equality with the data or values, which are presented via the line 121 by the limiting value storage GWSP to the comparison unit VGE. The comparison unit VGE communicates to the alarm counter unit ACE via the line 122 any failure to comply with the lower and upper limiting frequency value. After such a failure to comply, that is to say coming below or above the respective limiting values, three times in succession, the alarm counter unit ACE uses the signal "Alarm" conveyed by the line 123 to start the alarm driver ALT, which via the line 124 is connected with the 800 Hz clock signal "KAF" of the frequency dividing counter FTZ and for its part excites the loudspeaker LSP via the line 125. The alarm counter unit ACE starting the alarm driver ALT simultaneously communicates the alarm condition with the signal "$\overline{CInh}$" via the line 123a via the gate G9 and the line 126 to the control logic STL, which maintains this alarm condition for 0.5 second and then by issuing the control command "LA" to the alarm counter unit ACE via the line 127 terminates the alarm condition.

The setting of the lower and the upper limiting frequencies respectively is communicated to the control logic STL with the signal "$\overline{CInh}$" by the limiting value setter GWE via the line 128, the gate G9 and the line 126, following which the control logic STL starts a so-called pseudo-division. Simultaneously the signal "FProg" presented by the limiting value setter GWE via the line 128a to the gates G3/G4, ensures that the division result pulses do not pass via the lines 114 and 115 and respectively 115a to the display register AZR and, respectively, to the limiting frequency comparison register GVR. The signal "FProg" presented via the line 128a to the gates G3/G4 furthermore ensures that at the end of each division cycle the display register AZR and the limiting frequency comparison register GVR are caused to count up a value of 1 via the gates G3/G4 and the lines 115 and respectively 115a. The limiting value setter GWE furthermore by the application of a control signal "Store" via the line 129 at the limiting value storage GWSP presents those data to the limiting storage GWSP, which via the line 130 are presented from the limiting frequency comparison register GVR at the limiting value storage GWSP.

Since approximately 15 seconds after the last QRS complex received the whole system of the circuit is to change over into the standby operational mode, the time measuring counter ZM stops by dint of the signal "$\overline{KST}$" the clock generator TG of the clock unit TGE after the expiry of this time via the line 131a and via the line 131 sets the flip-flop FF5 of the standardising unit NE, which informs the control logic STL of its standardised condition with the signal "MC" provided via the line 132. The standardized condition of the flip-flop FF5 of the standardizing unit NE is cancelled by the control logic STL with the signal "$\overline{LA}$" via the line 133 as soon as a new incoming QRS complex is recognized.

In what follows the individual functions of the cardiac frequency measuring instrument in accordance with the invention are to be explained with reference to the circuitry in accordance with FIGS. 3 to 6.

THE INPUT AMPLIFIER

The ECG signal with a level of approximately 1 millivolt is detected via two stick-on electrodes E1 and E2 on the thorax of the patient, while as a neutral electrode VM use is made of the watch housing 11 with the metal wrist strap 12. The 1 millivolt ECG signal detected is transferred via two capacitors C1 and C2 capacitively to the input circuit of the operational amplifier OP1 connected as an active low pass filter of the first order so that any direct voltages are suppressed. The two diodes D1 and D2 connected in an anti-parallel fashion between the capacitors C1 and C2 prevent any damage to the difference input of the operational amplifier OP1 owing to high static voltages.

The input amplifier OP1 amplifies the input signal of 1 millivolt to a level of approximately 100 millivolts. The 100 millivolts signal is supplied via a passive high pass filter, consisting of the capacitor C5 and the resistors R7 and R8 to the input of the resonant amplifier OP2, which from the ECG selects the QRS complex and amplifies the QRS signal to a level of approximately 1 volt. The resonant amplifier OP2 has its output connected with a selective trigger amplifier OP3, which is coupled via a high pass filter and for its part forms a second order resonant amplifier. The trigger amplifier OP3 shapes the QRS complex recognized by the resonant amplifier OP2 to form a square rectangular signal with a level of approximately 2 volts.

The resonant amplifier OP2 connected as a high pass filter operates with a frequency of 16 Hz so that slow events such as for example artefacts due to movement are not amplified and accordingly are not further processed.

BRINGING INTO SYNCHRONISM

On recognizing a QRS complex, that is to say when the trigger amplifier OP3 produces a rectangular signal, via the gate G16, operating as a level converter, and with which the 2 volt rectangular signal is increased to a 3.6 volt logic level, the monoflop M1 is started. The monoflop M1 runs for approximately 40 milliseconds and prevents accordingly any double triggering of the synchronising logic by an excessively large QRS complex which could produce two output pulses in the trigger amplifier OP3. Simultaneously with the monoflop M1 the monoflop M2 starts and runs for 5 microseconds. The monoflop M2 starts via the gate G1 of the clock TG and produces together with the set flip-flop FF1 the pulse PA and with its rear edge resets the flip-flop FF1 via the input CP. The output pulse $\overline{PA}$ of the gate G18 causes via the gate G0 cancellation of the frequency dividing counters FTZ1 and FTZ2 so that they stand at 0, together with the non-set flip-flop FF2 via its output Q produces the pulse PA1 and with its rear edge sets the flip-flop FF2 at Count.

The pulse PA1 causes cancellation in the time measuring counter ZM, consisting of ZM1, ZM2 and ZM3, and also the frequency dividing counter FTZ5 so that they are reset at 0. Furthermore the pulse PA1 via the S input sets the flip-flop FF4, which serves for recognition of failure to comply with the set limiting frequency values.

TIME MEASUREMENT

At the end of the pulse PA1 measurement of the time interval between two QRS complexes begins. The time measuring counter ZM is caused to count with a frequency of 125 Hz. This frequency of 125 Hz is supplied by the central beat generator or clock TG, which is constructed so that it can start itself or be started extrinsecally via the gate G1 and runs with ± 1% accuracy of the frequency of 30 kHz, which is formed by the frequency dividing counter FTZ1 dividing by 10, the adjustable frequency dividing counter FTZ2 dividing by 12 or 15 and which is set at division by 12, and the dividing by two frequency dividing counter FTZ5.

The next QRS complex again triggers the monoflop M2 and the monoflop M1 but however cannot use any pulse PA since the flip-flop FF1 is not set. The flip-flop FF1 is however set again by the rear edge of the pulse via the CP input. The following QRS complex, that is to say the third QRS complex in this manner of numeration, again triggers the monoflop M1 and the monoflop M2. Since now the flip-flop FF1 is set, the monoflop M2 again produces a pulse PA. The pulse $\overline{PA}$ inverted by the gate G18 cannot produce any pulse PA1 since the flip-flop FF2 is set so that the pulse $\overline{PA}$ sets the flip-flop FF3 via the gate G2 and accordingly starts the computing process.

The rear edge of the pulse PA or respectively $\overline{PA}$ resets the flip-flop FF2, which is accordingly enabled for a new synchronisation operation. The rear edge of the pulse MA at the Q output of the monoflop M2 cannot reset the flip-flop FF1, because the enabling input K of the flip-flop FF1 has passed to 0 owing to the setting of the flip-flop FF3.

COMPUTATION

The computing operation is started by the setting of the flip-flop FF3. The frequency dividing counter FTZ2, which can divide by 12 or 15, is set for division at 15 by setting to zero of the flip-flop FF2. Accordingly the output frequency of the frequency dividing counter FTZ2 is changed to a value of 200 Hz. By means of the pulse $\overline{PA}$ the frequency dividing counters FTZ1 and FTZ2 are cancelled again. The set flip-flop FF3 prevents via the enable input E of the time measuring counter ZM1 any further counting by the time measuring counter ZM consisting of the three counters ZM1, ZM2 and ZM3 and enables the frequency dividing counters FTZ3 and FTZ4, which are held via their R inputs at 0 by the setting of the flip-flop FF3 at 0.

The flip-flop FF3 furthermore enables the division counters DiCo1, DiCo2 and DiCo3 held at 0 via their MR inputs. Furthermore the flip-flop FF3 holds the monoflop M2 via its CD input at 0 so that a triggering of the monoflop M2 will not be possible during the computing cycle.

The individual computing units DiCo1, DiCo2 and DiCo3 of the division counter DiCo, which obtain their time data from the time measuring counter ZM via the respective inputs DP1, DP2, DP3 and DP4, now carry out the division in accordance with the initially mentioned formula display value = $15\,000/t_M$ The number, corresponding to the division result of pulses is detected at the output "0" of the division counter DiCo1 as count display register or CAR pulses. The 15,000 pulses used as a constant in the formula are counted of via the frequency dividing counters FTZ1, FTZ2, FTZ3 and FTZ4. At the end of the 15,000 pulses via the input B the monoflop M3 is started, which also runs for approximately 5 microseconds and terminates the computing cycle.

ORGANISATION AND DISPLAY OF THE DIVISION RESULT

The division result is formed in the registers AZR1, AZR2 and AZR3 of the display register AZR. The display register AZR was reset by the flip-flop FF2 during time measurement via the respective "R" inputs at 0 and is now caused to count by the pulses CAR, which arrive via the gates G3 and G4 at the C input of the display register AZR1. The display register AZR operates in BCD code and consequently makes available to the display driver AT, consisting of the driving units AT1, AT2 and AT3, directly displayable values.

With the triggering of the monoflop M3 the load display pulse LA is produced. With this pulse LA the instantaneous measuring frequency value, which is present in the display register AZR at the respective outputs Q1 to Q4 of the display registers AZR1 to AZR3 and is accordingly also available at the inputs A, B, C, D of the display drivers AT1, AT2 and AT3, is taken into the display driver AT and is accordingly displayed via the respective segment lines $a$ to $g$.

Independently of the frequency value indicated by the display 13 the 40 ms pulse of the monoflop M1 by dint of the signal Syst via the gate G13 and the signal DOPP brings about a flashing of the double point 14 of the display in the systolic rhythm of the cardiac frequency.

MONITORING OF MAINTENANCE OF THE FREQUENCY RANGE SET

Simultaneously with the counting up by the display register AZR the limiting frequency comparison register GVR, consisting of the registers GVR1 and GVR2 is caused to count up, which was previously subject to cancellation by the flip-flop FF2 via the respective "R" inputs so as to be set at 0. In the limiting frequency comparison register GVR there then follows the establishment of the division result so that the comparison is possible with only two 4-bit comparators in the frequency range of 0 to 255.

The division result becoming established in the limiting frequency comparison register GVR is applied via the respective outputs Q1 to Q4 of the registers GVR1 and GVR2 to the respective inputs A0 to A3 of the two comparators VG1 and, respectively VG2 of the comparator VG. The result of division formed is investigated by the comparator VG together with the storage min consisting of the storage units Smin1 and Smin2 for the lower limiting frequency as regards equality and the comparators VG1 and VG2 are connected at their respective inputs B0 to B3 by dint of the signal present at the respective Dis inputs of the storages Smin1 and Smin2 with the respective outputs Q0 to Q3 of the storages Smin1 and Smin2.

If during this counting operation equality is detected between the counted value and the stored value, that is to say the lower limiting frequency value, the "A=B" output of the comparator VG2 is changed over to "high" and accordingly the K input of the flip-flop FF4 is changed to "high".

As a result the next positive edge of the 30 kHz clock produced by the clock TG sets the flip-flop FF4 at 0. As a result owing to the signal present at the respective Dis inputs of the storages Smin1 and Smin2, the respective inputs B0 to B4 of the comparators VG1 and VG2 are separated from the storage Smin and the respective outputs Q0 to Q3 of the storages Smax1 and Smax2 for the upper limiting frequency are connected with the respective inputs B0 to B4 of the comparators VG1 and VG2, since the corresponding signal from the Q output of the flip-flop FF4 is applied to the respective Dis inputs of the storages Smax1 and Smax2.

Following this the register contents of the limiting frequency comparison register GVR is compared with the storage contents of the storage Smax for the upper limiting frequency and investigated as to whether A exceeds B, that is to say it is checked whenever the limiting frequency comparison register GVR has a higher value than the stored upper limiting frequency. If the stored upper limiting frequency is exceeded, the "A > B" output of the comparator VG2 changes over to "high" makes possible owing to the driving of the enabling input J of the flip-flop FF4 the setting of the flip-flop FF4 by the clock T6. It does become clear that the flip-flop FF4 is only at 0 if normal frequencies are measured and counted, that is to say the frequencies lying between the upper and the lower limiting frequencies.

The pulse LA, which transports the division result via the respective Ld inputs into the display drivers AT1 and AT3 tends to cause the alarm counter AC to count forwards via the C input. If however the flip-flop FF4 is not set, since a frequency value lying between the lower limiting frequency and the upper limiting frequency has been detected, the alarm counter AC is set via its "R" input via the gate G5 and R input to 0.

OPERATION OF ALARM

The alarm counter AC is not set at zero three times in succession by the flip-flop FF4 via the gate G5, the alarm counter AC reaches with the front edge of the third LA pulse the position "3", which via the gates G6 and G7 gives rise to the signal "Alarm". The "Alarm" signal allows the passage of the 800 Hz clock of the KAF signal present at the Q2 output of the frequency dividing counter FTZ2 at the gate G8. The signal KAF allowed to pass then excites [via] via the drivers T1, T2 and T3 and the decoupling capacitor C17. [the loudspeaker LSP].

The "3" position further<u>more</u> produces via the gate G9 the Count inhibit pulse $\overline{\text{CJnh}}$ which ensures that the flip-flop FF3 is not reset with the rear edge of the $\overline{\text{LA}}$ pulse and accordingly there is no possibility of renewed synchronisation to a new QRS complex by the triggering of the monoflop M2. Owing to the failure to reset the flip-flop FF3 the computing mode remains set.

The "Alarm" signal present at the Inh input of the division counter DiCo1 and coming from the output of the inverter G7 however ensures that the division counter does not provide any CAR pulses and therefore ensures that the result in the display register AZR and in the limiting frequency comparison register GVR is not falsified.

After the expiry of the computing cycle lasting for 15,000 pulses, during which the acoustic warning signal is produced via the loudspeaker LSP, the LA signal then generated causes by means of its front edge the alarm counter AC to count further to the position "4", which in the case of the decoding selected corresponds to its "0" position. As a result the signals Alarm and Count-Inhibit are withdrawn, the alarm sound ceases and the rear edge of the $\overline{LA}$ pulse resets the flip-flop FF3 via the CP input so that the possibility of a new synchronisation is presented.

STANDBY OPERATION

On termination of a computing cycle, that is to say with the resetting of the flip-flop FF3 by the rear edge of a $\overline{LA}$ pulse the time measuring counter ZM is enabled via the E input of the counter ZM1 for counting forwards. If now no new QRS complex starts the monoflop M1 and accordingly the monoflop M2 within a period of time lasting for approximately 15 seconds, and accordingly it does not set the time measuring counter ZM at zero, the time measuring counter ZM counts until the output Q3 of the time measuring counter ZM3 passes over to "high". This "high" signal produces via the inverter G10 the $\overline{KST}$ signal, which via the CD input stops the clock TG. The $\overline{KST}$ signal provides via the gate G11 the master clear signal MC. The MC signal produces via the S input the setting of the flip-flop FF5, which via the respective B1 inputs cancels the display at the display drivers AT1, AT2 and AT3 so that no frequency value is now displayed.

By switching off the beat generator or clock TG the supply current in the logic circuitry is reduced from approximately 35 microamperes to approximately 15 microamperes and does not even amount to 50% of the normal operational current. The master clear signal MC is produced on switching on, that is to say on setting the voltage supply via the RC member with the resistor R23 and the capacitor C16 at the second input of the gate G11. The MC signal standardises the overall logic so that at any time a new synchronisation can be carried out.

SETTING OF THE LIMITING FREQUENCIES

The setting of the upper and the lower limiting frequency values is carried out in standby operation with the help of the two reed contacts Reedmax and Reedmin, which can be closed independently of each other with externally applied magnets. Closing of the reed contact Reedmax the signal $\overline{KProg}$, which when the reed contact Reedmax is not closed is held via a high ohmic resistor R25 to the value VCC of the supply voltage, is switched on with respect to the signal $\overline{EProg}$. The latter signal is the signal present at the Q1 output of the time measuring counter ZM1, which in standby operation in any case lies at 0 so that also the signal $\overline{KProg}$ passes to 0. The signal $\overline{KProg}$ sets via the S input the flip-flop FF6 consisting of the gates G14 and G15 and triggers via the B input the monoflop M2. Simultaneously the flip-flop FF6 sets with the pulse FProg the flip-flop FF1 via the S input so that the monoflop M2 and the flip-flop FF1 produce the pulse PA and, respectively $\overline{PA}$.

Since in standby operation the $\overline{KST}$ pulse is always still present at the gate G11, the flip-flop FF2 is reset by the MC pulse produced at the gate G11 so that the gate G17 produces the pulse PA1. The pulse PA1 standardises all counter units ZM1, ZM2 and ZM3 of the time measuring counter ZM and the Q3 output of the time measuring counter ZM3 is set at 0 so that the signal $\overline{KST}$ and accordingly the MC signal disappear.

As soon as the $\overline{KST}$ signal is removed, the clock TG or clock generator is enabled and the rear edge of the signal produced at the $\overline{Q}$ output of the monoflop M2 can start the clock TG via the gate G1 and the input B. The rear edge of PA and, respectively $\overline{PA}$ sets the flip-flop FF2 via the CP input and the flip-flop FF2 cancels the display register AZR and the limiting frequency comparison register GVR. The clock scaled down to 125 Hz by the frequency dividing counters FTZ1, FTZ2 and FTZ5, of the clock TG now causes the time measuring counter ZM to count forwards. The signal $\overline{EProg}$ received at the output Q1 of the time measuring counter ZM1 accordingly passes back to 0 after "high". When the reed contact Reedmax is closed furthermore with the signal $\overline{EProg}$ the signal $\overline{KProg}$ passes to "high" and back again to 0 and the negative flank produced as a result of the signal $\overline{KProg}$ triggers the monoflop M2 via its B input.

The triggered monoflop M2 and the flip-flop FF1 still set by the signal FProg via the S input produce the pulse PA and, respectively $\overline{PA}$. Since the flip-flop FF2 is set, via the gate G2 and the S input the flip-flop FF3 is set. The time measuring counter ZM is stopped and the signal $\overline{EProg}$ remains active.

The binary counters DiCo1, DiCo2 and DiCo3 of the division counter now carry out a computing operation though however the CAR pulses of the division result cannot, as is the case with a "normal" computing operation cause the display register AZR to count forwards via the gates G3 and G4, since the signal $\overline{KProg}$ at the gate G3 blocks this path. The display registers AZR and GVR thus remain at zero. If after 0.5 seconds the clock TG has produced 15,000 pulses, the monoflop M3 produces a load display pulse LA. This LA pulse transports, as is the case with every computing operation, the respective values of the display register AZR1 to AZR3 into the display drivers AT1 to AT3 and with the rear edge of the $\overline{LA}$ pulse resets the flip-flop FF5 via the CP input. The flip-flop FF5 enables via the B1 input the display at the display drivers AT1, AT2 and AT3 so that the display indicates the value 000.

Since the reed contact Reedmax is still closed and accordingly the gate G12 is enabled by it, the $\overline{LA}$ pulse produces the Store pulse, which is present at the respective store enable inputs ST of the storages Smax1 and Smax2 and when the reed contact Reedmin is closed is also presented to the respective ST inputs of the storages Smin1 and Smin2. The consequence of this is that the signals presented at the respective Q1 to Q4 outputs of the register GVR1 and GVR2 and the respective D0 to D3 inputs of the storages Smax1 and Smax2 and, respectively, of the storages Smin1 and Smin2 and accordingly the value present in the limiting frequency comparison register GVR is taken over into the storage for the upper and, respectively lower limiting frequency.

The Store pulse furthermore resets via the R input the flip-flop FF4 and accordingly prevents the giving of alarm. Furthermore the $\overline{LA}$ signal attempts via the $\overline{R}$ input to reset the flip-flop FF6, since however the signal $\overline{KProg}$ is still active, the signal $\overline{LA}$ can only set the Q output of the flip-flop FF6 at "high" for the duration of the pulse LA and, respectively $\overline{LA}$. The negative edge, which is produced at the end of the pulse LA and, respectively $\overline{LA}$ at the $\overline{Q}$ output of the flip-flop FF6, causes the display register AZR and the limiting frequency comparison register GVR to count up by one digit. The rear edge of $\overline{LA}$ attempts to reset via the CP input the flip-flop FF3 something which however — as already explained in the part supra headed operation of alarm — is prevented by the count inhibit signal $\overline{CInh}$, which is formed by the flip-flop FF6 via the gate G9. Accordingly the computing cycle is repeated.

On the basis of the gate G3 disenabled by the signal $\overline{KProg}$ further counting is prevented again both as regards the display register AZR and also the limiting frequency comparison register GVR so that the pulses LA and Store in the display registers AZR1 to AZR3 and the display drivers AT1 to AT3 respectively produce the value 001. The display register AZR and the limiting frequency comparison register GVR are now counted forwards by one digit. This operation is repeated till the reed contact Reedmax is opened by removal of the external magnet. Then owing to the pulse $\overline{LA}$ the signal FProg is cancelled and the count inhibit signal $\overline{CInh}$ disappears and the rear edge of $\overline{LA}$ resets the flip-flop FF3.

Now the logic circuitry again awaits the next QRS complex in order to begin with renewed synchronisation; if however the next QRS complex does not arrive within approximately 15 seconds, the digital circuit automatically switches back to standby operation again.

It is to be pointed out that all features specified in the above description are significant for the invention.

I claim:

1. A cardiac frequency measuring instrument including a minaturized digital circuit frequency measuring device adapted to be carried on the arm of a patient, measuring electrodes adapted to be attached to the body of the patient for generating an electrical signal in response to the heart beat frequency of the patient, a cable for carrying electrical signals generated by said electrodes connecting the frequency measuring device with said measuring electrodes carried on the body, an optical display electrically coupled to said frequency measuring device for visually displaying the frequency measured by said frequency measuring device and corresponding to the heart beat frequency of the patient, and a housing means having the size of a wrist watch for containing said frequency measuring device and said optical display, said cardiac frequency measuring instrument requiring relatively low electrical power consumption for digital measurement and display of the cardiac frequency, said frequency measuring device including a resonant amplifier, connected as a high pass filter, for automatically suppressing the amplification and display of motional artifacts, thereby reducing error between the displayed heart beat frequency and the actual heart beat frequency; said cardiac frequency measuring instrument including a standby means for assuming a standby configuration having a power consumption only a fraction of the normal power consumption, said standby means being responsive to an absence of electrical signals representing the heart beat frequency so that said cardiac frequency measuring instrument automatically assumes said standby configuration whenever there is an absence of electrical signals representing the heart beat frequency from said measuring electrodes for a predetermined time interval.

2. The structure as set forth in claim 1 wherein said housing means includes an arm strap for attaching said housing means to the arm of the patient and said housing means includes a conductive path adapted to be between the body of the patient and the interior of said housing means thereby establishing a neutral electrode, said conductive path being electrically connected to said frequency measuring device.

3. The structure as set forth in claim 1 wherein said optical display includes LCD means for displaying digits for numerical display of frequency values.

4. The structure as set forth in claim 3 characterized in that said cardiac frequency measuring instrument includes means for indicating a drop in the operational voltage below a predetermined threshold voltage with a decrease in luminosity of said optical display.

5. The structure as set forth in claim 3 wherein said optical display includes at least one flashing point, and said frequency measuring device includes means for electrically driving said flashing point so that said flashing point flashes in the measured systolic rhythm of the cardiac frequency.

6. The structure as set forth in claim 3 wherein said optical display includes a numerical display including digits for representing the hundreds and tens digits of the heart beat frequency of the patient and said flashing point is positioned between the hundreds and tens digits of the numerical display.

7. The structure as set forth in claim 1 wherein said frequency measuring device includes an alarm device means adapted to respond to an upper and a lower limiting frequency, thereby providing an acoustic signal on failure of the heart beat frequency to comply with the limiting frequencies.

8. The structure as set forth in claim 7 wherein said alarm device means is responsive to upper and lower limiting frequencies having magnitudes set at any integral values between 0 and 255 including 0.

9. The structure as set forth in claim 7 wherein said frequency measuring device includes a switch means for setting the upper and lower limiting frequencies and a clock having a predetermined clock beat, a register, electrical storage means and a counter, said clock, said register, said electrical storage means and said counter being coupled to respond to the actuation of said switch means to drive said clock, and set said register, said electrical storage means and said counter at zero, said clock being connected to said counter and said counter being connected to said register so that with said predetermined clock beat brings about a continuous pulse sequence for causing forward counting of frequency values within said frequency measuring device, said register being connected to said electrical storage means and the last of such frequency values counted being stored as a limiting frequency in said storage means.

10. The structure as set forth in claim 9 wherein said switch means includes a reed contact switch adapted to be closed by an external magnet so that a sufficiently close presence of the external magnet to the reed contact switch drives said clock, sets said register, said storage means and said counter at zero.

11. The structure as set forth in claim 9 wherein said frequency measuring device includes selection means for decoupling said optical display from electrical signals generated by said measuring electrodes and coupling said optical display to signals representing the forward counting of frequency values during setting of limiting frequencies so that said optical display indicates the value of the counted frequency.

12. The structure as set forth in claim 9 wherein said frequency measuring device includes means for deactuating said alarm device means during forward counting of frequency values within said frequency measuring device.

13. The structure as set forth in claim 1 wherein said frequency measuring device is made up of C-MOS components.

14. The structure as set forth in claim 13 wherein said frequency measuring device has a voltage supply from a long life mercury cell with a constant voltage.

* * * * *

UNITED STATES PATENT AND TRADEMARK OFFICE
CERTIFICATE OF CORRECTION

PATENT NO. : 4,108,166
DATED : August 22, 1978
INVENTOR(S) : Walter Schmid

It is certified that error appears in the above-identified patent and that said Letters Patent are hereby corrected as shown below:

Column 4; line 55:
　"reasure" should be --reassure--

Column 5; line 66:
　"athlets" should be --athletes--

Column 6; line 4:
　"sthe" should be --the--

Column 7; line 21:
　"acoustic signal" should be --acoustic warning signal--

Column 7; line 62:
　"an" should be --a--

Column 14; line 32:
　"an" should be --a--

Column 15; line 49:
　"Q" should be --$\overline{Q}$--

Column 16; line 8:
　"Q" should be --$\overline{Q}$--

Column 17; line 50:
　"and" should be --are--

Column 17; line 60:
　"presetenable" should be --presettable--

Column 18; line 3:
　"counter" should be --counters--

Column 20; line 2:
　"Q" should be --$\overline{Q}$--

UNITED STATES PATENT AND TRADEMARK OFFICE
CERTIFICATE OF CORRECTION

PATENT NO. : 4,108,166

DATED : August 22, 1978

INVENTOR(S) : Walter Schmid

It is certified that error appears in the above-identified patent and that said Letters Patent are hereby corrected as shown below:

Column 23; line 38:
   "square rectangular" should be --square or rectangular--

Column 25; line 59:
   "min" should be --Smin--

Column 26; line 21:
   "whenever" should be --whether--

Column 26; line 36:
   "forwards" should be --forward--

Column 26; lines 51 through 54:

"The signal KAF allowed to pass then excites [via] via the drivers T1, T2 and T3 and the decoupling capacitor C17 [the loudspeaker LSP]." should be --The signal KAF is allowed to pass then excites via the drivers T1, T2 and T3 and the decoupling capacitor C17, loudspeaker LSP.--

Column 27; line 18:
   "forwards" should be --forward--

Column 27; line 26:
   "provides" should be --produces--

Column 28; line 14:
   "forwards" should be --forward--

Column 28; line 32:
   "forwards" should be --forward--

UNITED STATES PATENT AND TRADEMARK OFFICE
CERTIFICATE OF CORRECTION

PATENT NO. : 4,108,166

DATED : August 22, 1978

INVENTOR(S) : Walter Schmid

It is certified that error appears in the above—identified patent and that said Letters Patent are hereby corrected as shown below:

Column 29; line 17:
"forwards" should be --forward--

Column 30; line 19:
"3" should be --5--

Signed and Sealed this

Fifteenth Day of May 1979

[SEAL]

Attest:

RUTH C. MASON
*Attesting Officer*

DONALD W. BANNER
*Commissioner of Patents and Trademarks*